(12) United States Patent
Hasan et al.

(10) Patent No.: US 10,426,388 B2
(45) Date of Patent: Oct. 1, 2019

(54) PREDICTION OF TUMOR RECURRENCE BY MEASURING OXYGEN SATURATION

(71) Applicant: THE GENERAL HOSPITAL CORPORATION, Boston, MA (US)

(72) Inventors: Tayyaba Hasan, Boston, MA (US); Srivalleesha Mallidi, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 338 days.

(21) Appl. No.: 15/114,906

(22) PCT Filed: Feb. 2, 2015

(86) PCT No.: PCT/US2015/014068
§ 371 (c)(1),
(2) Date: Jul. 28, 2016

(87) PCT Pub. No.: WO2016/076905
PCT Pub. Date: May 19, 2016

(65) Prior Publication Data
US 2017/0135615 A1    May 18, 2017

Related U.S. Application Data

(60) Provisional application No. 62/079,782, filed on Nov. 14, 2014, provisional application No. 61/934,210, filed on Jan. 31, 2014.

(51) Int. Cl.
*A61B 5/1455* (2006.01)
*A61B 5/00* (2006.01)
(Continued)

(52) U.S. Cl.
CPC ........ *A61B 5/14551* (2013.01); *A61B 5/0095* (2013.01); *A61B 5/14542* (2013.01);
(Continued)

(58) Field of Classification Search
CPC . A61B 5/0095; A61B 5/1455; A61B 5/14551; A61B 5/14552; A61B 5/4848; A61B 5/7275; A61B 5/0073; A61B 5/055
See application file for complete search history.

(56) References Cited

U.S. PATENT DOCUMENTS 7,715,901 B2   5/2010  Salomon et al.
2003/0008857 A1  1/2003  Hunt et al.
(Continued)

OTHER PUBLICATIONS

PCT International Search Report for PCT/US15/14068, dated Apr. 21, 2015, 1 page.

*Primary Examiner* — Eric F Winakur
*Assistant Examiner* — Chu Chuan Liu
(74) *Attorney, Agent, or Firm* — Tarolli, Sundheim, Covell & Tummino LLP

(57) ABSTRACT

A method for measuring differential blood oxygen saturation in a solid tumor is described that includes the steps of obtaining a first oxygenation image of a solid tumor before, during, or immediately after a administration of vascular therapy; obtaining a second oxygenation image of the solid tumor after a devascularization time period; and determining a differential blood oxygen saturation value by comparing the first oxygenation image and the second oxygenation image. The differential blood oxygen saturation value can be compared to a blood oxygen saturation necrosis value to provide a prognosis for tumor recurrence, or to guide of the tumor.

19 Claims, 9 Drawing Sheets

(51) Int. Cl.
   *A61B 5/145*   (2006.01)
   *A61N 5/06*    (2006.01)
   *G06T 7/00*    (2017.01)
   *G16H 50/30*   (2018.01)
   *G16H 30/40*   (2018.01)
   *G16H 50/20*   (2018.01)
   *G16H 20/40*   (2018.01)
   *A61B 5/055*   (2006.01)

(52) U.S. Cl.
   CPC .......... *A61B 5/4848* (2013.01); *A61B 5/7275* (2013.01); *A61N 5/062* (2013.01); *G06T 7/0016* (2013.01); *G16H 20/40* (2018.01); *G16H 30/40* (2018.01); *G16H 50/20* (2018.01); *G16H 50/30* (2018.01); *A61B 5/0073* (2013.01); *A61B 5/055* (2013.01); *A61B 2505/05* (2013.01); *A61B 2576/00* (2013.01); *G06T 2207/30096* (2013.01)

(56) References Cited

U.S. PATENT DOCUMENTS

| | | |
|---|---|---|
| 2008/0221647 A1 | 9/2008 | Chamberland et al. |
| 2012/0027679 A1 | 2/2012 | Yamauchi et al. |
| 2016/0174886 A1* | 6/2016 | Shiraishi ............ A61B 5/14551 |
| | | 600/339 |

\* cited by examiner

PREDICTION OF TUMOR RECURRENCE BY MEASURING OXYGEN SATURATION

CROSS-REFERENCE TO RELATED APPLICATIONS

This application claims priority from U.S. Provisional Application Ser. No. 62/079,782, filed Nov. 14, 2014, the entire contents of which are incorporated herein by reference.

GOVERNMENT FUNDING

This invention was made with Government support under grant number NIHR01CA15617704 awarded by the National Institutes of Health and the National Cancer Institute. The Government has certain rights in the invention.

BACKGROUND

The structural, vascular, and metabolic heterogeneity of cancer biology confers substantial limitations to the effectiveness of standard cancer treatments, such as radiotherapy or chemotherapy resulting frequently in tumor recurrences. The recurrent disease can be aggressive and often resistant to standard treatments. For example in malignant glioblastoma, 90-95% tumors recur locally and less than 15% of these recurrent tumors show response to standard chemotherapy. De Bonis et al., 115(1):37-43 (2013). Indeed, there is no standard of care for recurrent glioblastoma. The cause of local recurrence is not entirely established and probably reflects the heterogeneity in tumor cells, tumor vasculature and hypoxia—all of which may play a major role, either individually or collectively, in resistance to standard therapies. Given these heterogeneities, information on change in tumor volume alone post-therapy is not predictive of therapy response or recurrence. Surrogate functional markers such as change in tumor vascular density, perfusion and metabolic activity occurring in the tumor due to therapy could provide better prediction of therapy response, aid in stratification of subjects and design of subsequent therapeutic interventions earlier in the disease management. Zhao et al., Journal of Nuclear Medicine; 50(2):239-49 (2009). Therefore importance of non-invasive imaging modalities that provide functional information in predicting therapy response is irrefutable. Tirkes et al., Radiographics; 33(5):1323-41 (2013).

Amongst the emerging vascular targeted therapies, Photodynamic therapy (PDT) is gaining popularity as it causes spatially localized tumor vascular destruction with minimal side effects. In PDT, photosensitizer (PS) preferentially accumulates in malignant tissue as a result of increased tumor vascular permeability and wavelength-specific light-activation of the PS, generates cytotoxic reactive species including oxygen species (ROS). ROS subsequently induces tumor cell and vascular destruction. PDT has temporal and spatial selectivity because (1) PS is accumulated in tumor tissue and its associated vasculature in a time-dependent manner and (2) light illumination can be regionally localized to the area of malignancy. Celli et al., Chem. Rev.; 110(5): 2795-838 (2010). Additional tumoral selectivity for the PS can be achieved through liposomal encapsulation or PS conjugation to targeting moieties such as antibodies. Currently, PDT is approved for several applications and is in clinical trials for other malignancies such as Cholangiocarcinoma (NCT01524146), Oropharyngeal Cancer (NCT01718223), Glioma (NCT01682746)16,20,27 and locally advanced pancreatic cancer (NCT01770132).

As with radio- and chemotherapy, heterogeneity in tumor oxygenation can result in variable PDT outcomes. Wilson et al., Lasers Med Sci.; 12(3):182-99 (1997); Woodhams et al., Photochem. Photobiol. Sci.; 6(12):1246 (2007); Henderson B W, Fingar V H., Cancer Research.; 47(12):3110-4 (1987). Besides the inherent erratic nature of tumor vasculature, the heterogeneity of tumor oxygenation is attributed to variations in inter-capillary distance, intra-vascular pO2, blood flow rates, and vascular permeability. Goel et al. Physiological Reviews, 91(3):1071-121 (2011); Diaz-Cano S J. IJMS.; 13(2):1951-2011 (2012); Hockel M, Vaupel P., J Natl Cancer Inst., 93(4):266-76 (2001). Studies such as those by Pogue et al. have shown that as a consequence of this variability, response to PDT treatment is also not homogeneous. Pogue et al., J. Biomed. Opt., 10(4):41206-6 (2005). PDT effectiveness depends, amongst other parameters, on the availability and consumption of oxygen in the target tissue during light delivery and therefore, monitoring of tumor oxygenation before, during, and after PDT could provide an early indication of the long-term treatment outcome.

Direct measurements of tissue oxygenation status during PDT were obtained with pO2 histography. Sitnik et al., British Journal of Cancer, 77(9):1386-94 (1998); Coutier et al., Radiat. Res., 158(3):339-45 (2002). However, microelectrodes are invasive and only sample volume adjacent to the electrode. Non-invasive optical imaging techniques such as reflectance spectroscopy and diffuse optical tomography used to monitor changes in blood oxygen saturation ($StO_2$), an indirect method to represent tissue oxygenation status, have been promising. Woodhams et al., British Journal of Cancer, 91(4):788-94 (2004); Amelink et al., Journal of Photochemistry & Photobiology, B: Biology, 79(3):243-51 (2005); Yu G., Clinical Cancer Research, 11(9):3543-52 (2005); Wang et al., Cancer Research. October 15; 64(20): 7553-61 (2004); Pham et al., Photochemistry and Photobiology. Wiley Online Library; 73(6):669-77 (2001); Kostenich et al., Cancer Letters, 219(2):169-75 (2005); Thompson et al., Appl Opt., 44(19):4023-31 (2005); Sunar et al., Opt Express.; 18(14):14969 (2010). However, these have not provided 3D information on the tumor $StO_2$ heterogeneity that could play a major role in determining PDT outcome.

Blood oxygenation level dependent (BOLD) contrast MRI was also demonstrated for use in PDT, however it was sensitive only to deoxygenated hemoglobin changes in T2* relaxation time and has ~1 mm spatial resolution. Gross et al., Nature Medicine, 9(10):1327-31 (2003); Kim S-G, Ogawa S., J Cereb Blood Flow Metab., 32(7):1188-206 (2012). Advances in optical and acoustic technologies have led to an increase interest in the use of photoacoustic phenomena for biomedical imaging. This is due to the fact that photoacoustic imaging (PAI) has the sensitivity of optical imaging and yields a 3D atlas of the tumor blood oxygenation status at resolutions equal to ultrasound imaging. Xu M, Wang L V. Photoacoustic imaging in biomedicine. Review of Scientific Instruments; 77(4):041101 (2006). PAI uses a pulsed laser to induce localized thermoelastic expansion of optical absorber (such as hemoglobin) that generates acoustic waves. The generated photoacoustic waves are detected using an ultrasound transducer. Multi-wavelength PAI can provide $StO_2$ and total hemoglobin concentration (HbT) maps without the use of exogenous contrast agents as oxygenated and deoxygenated hemoglobin have different optical absorption properties. Zhang et al., Nat Biotechnol., 24(7):848-51 (2006); Zackrisson et al., Cancer Research, 74(4):979-1004 (2014).

SUMMARY OF THE INVENTION

Selection and design of individualized treatments remains a key goal in cancer therapeutics; prediction of response and tumor recurrence following a given therapy provides a basis for subsequent personalized treatment design. The inventors demonstrate an approach towards this goal with the example of photodynamic therapy (PDT) as the treatment modality and photoacoustic imaging (PAI) as a non-invasive, response and disease recurrence monitor in a murine model of glioblastoma (GBM). PDT is a photochemistry-based, clinically used technique that consumes oxygen to generate cytotoxic species thus causing changes in blood oxygen saturation ($StO_2$). It is hypothesized that this change in $StO_2$ can be a surrogate marker for predicting treatment efficacy and tumor recurrence. PAI is a technique that can provide a 3D atlas of tumor $StO_2$ by measuring oxygenated and deoxygenated hemoglobin. The inventors demonstrate that tumors responding to PDT undergo approximately 85% change in $StO_2$ by 24-hrs post-therapy while there is no significant change in $StO_2$ values in the non-responding group. Furthermore, the 3D tumor $StO_2$ maps predicted if a tumor was likely to regrow at a later time point post-therapy. Information on the likelihood of tumor regrowth that normally would have been available only upon actual regrowth (10-30 days post treatment) in xenograft tumor model, was available within 24-hrs of treatment using PAI, thus making early intervention a possibility. Given the advances and push towards availability of PAI in the clinical settings, the results of this study encourage applicability of PAI as an important step, to guide and monitor therapies (e.g. PDT, radiation, anti-angiogenic) involving a change in $StO_2$.

BRIEF DESCRIPTION OF THE FIGURES

The present invention may be more readily understood by reference to the following figures, wherein.

DETAILED DESCRIPTION OF THE INVENTION

Figure 1:
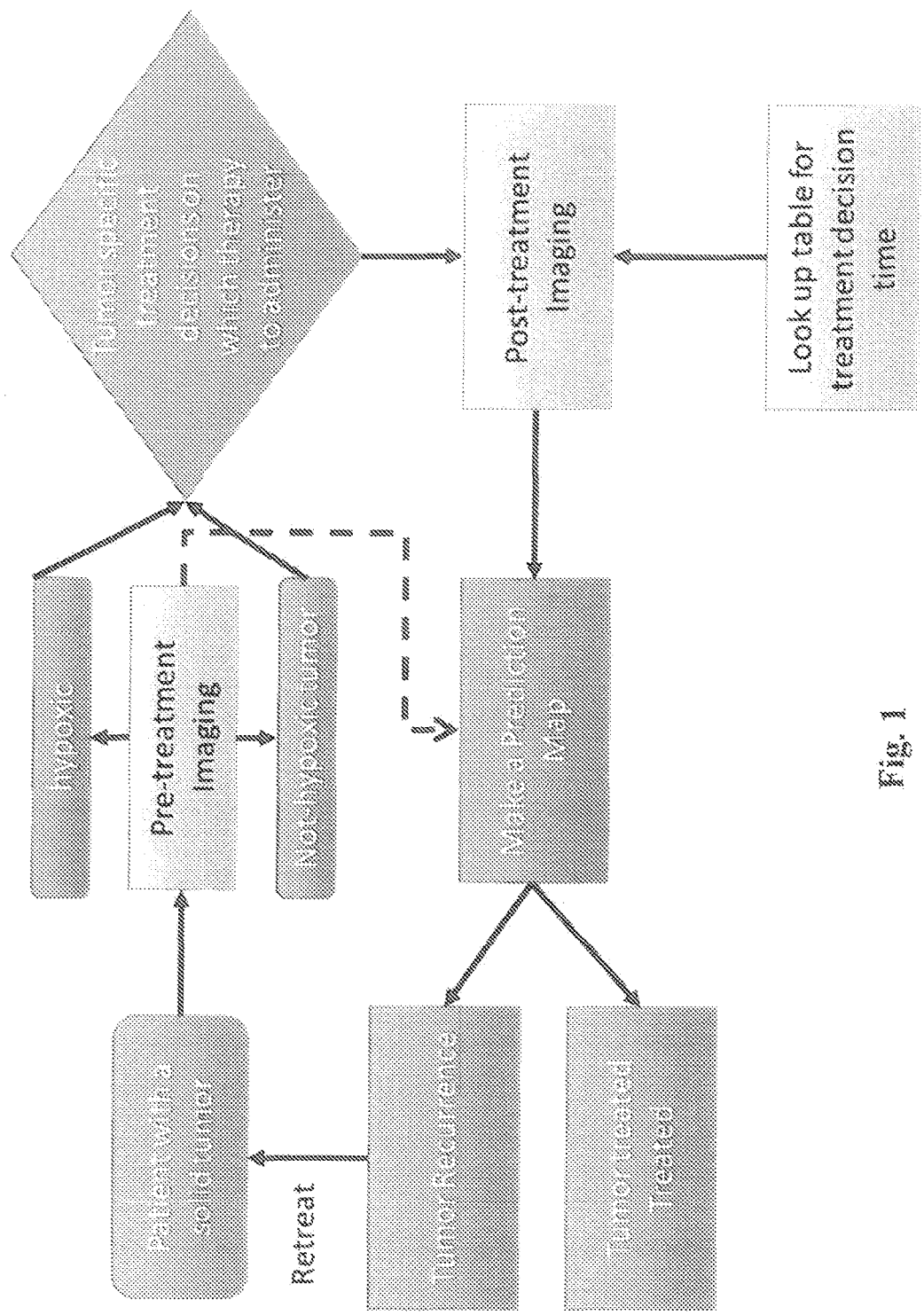
FIG. 1 is a flow diagram illustrating a method for treating a solid tumor in accordance with an aspect of the present invention

The present invention provides a method of differentiating responders from non-responders for those receiving vascular therapy for treatment of a solid tumor. The method involves measuring the differential blood oxygen saturation in a solid tumor by comparing an oxygenation image obtained after tumor devascularization with an oxygenation image obtained earlier, in which a decrease in blood oxygen saturation indicates the subject is a responder for the vascular therapy administered.

Definitions

As used herein, the term "diagnosis" can encompass determining the likelihood that a subject will develop a disease, or the existence or nature of disease in a subject. The term diagnosis, as used herein also encompasses determining the severity and probable outcome of disease or episode of disease or prospect of recovery, which is generally referred to as prognosis). "Diagnosis" can also encompass diagnosis in the context of rational therapy, in which the diagnosis guides therapy, including initial selection of therapy, modification of therapy (e.g., adjustment of dose or dosage regimen), and the like.

As used herein, the term "prognosis" refers to a prediction of the probable course and outcome of a disease, or the likelihood of recovery from a disease. Prognosis is distinguished from diagnosis in that it is generally already known that the subject has the disease, although prognosis and diagnosis can be carried out simultaneously. In the case of a prognosis for a subject having a solid tumor, the prognosis categorizes the relative severity of the tumor and/or the response of the tumor to initial therapy, which can be used to guide selection of appropriate therapy or subsequent therapy.

A "risk" is understood to be a number related to the probability that a subject or a patient will develop or arrive at a certain disease outcome. The term "risk" in the context of the present invention is not meant to carry any positive or negative connotation with regard to a patient's wellbeing but merely refers to a probability or likelihood of an occurrence or development of a given condition.

The term "clinical data" relates to the entirety of available data and information concerning the health status of a patient including, but not limited to, age, sex, weight, menopausal/hormonal status, etiopathology data, anamnesis data, data obtained by in vitro diagnostic methods such as histopathology, blood or urine tests, data obtained by imaging methods, such as x-ray, computed tomography, MRI, PET, spect, ultrasound, electrophysiological data, genetic analysis, gene expression analysis, biopsy evaluation, intraoperative findings.

As used herein, the terms "treatment," "treating," and the like, refer to obtaining a desired pharmacologic or physiologic effect. The effect may be therapeutic in terms of a partial or complete cure for a disease or an adverse effect attributable to the disease. "Treatment," as used herein, covers any treatment of a disease in a mammal, particularly in a human, and can include inhibiting the disease or condition, i.e., arresting its development; and relieving the disease, i.e., causing regression of the disease.

Prevention or prophylaxis, as used herein, refers to preventing the disease or a symptom of a disease from occurring in a subject which may be predisposed to the disease but has not yet been diagnosed as having it (e.g., including diseases that may be associated with or caused by a primary disease). Prevention may include completely or partially preventing a disease or symptom.

The term therapy, as used herein, encompasses activity carried out to treat a disease. The specific activity carried out to conduct therapy can include use of surgery, radiotherapy, hormonal therapy, chemotherapy, or the use of one or more therapeutic agents (e.g., anticancer agents).

The terms "therapeutically effective" and "pharmacologically effective" are intended to qualify the amount of an agent which will achieve the goal of improvement in disease severity and the frequency of incidence over treatment of each agent by itself, while avoiding adverse side effects typically associated with alternative therapies. The effectiveness of treatment may be measured by evaluating a reduction in tumor load or decrease in tumor growth in a subject in response to the administration of anticancer agents. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

The terms "individual," "subject," and "patient" are used interchangeably herein irrespective of whether the subject has or is currently undergoing any form of treatment. As used herein, the term "subject" generally refers to any vertebrate, including, but not limited to a mammal. Examples of mammals including primates, including simians and humans, equines (e.g., horses), canines (e.g., dogs), felines, various domesticated livestock (e.g., ungulates, such as swine, pigs, goats, sheep, and the like), as well as domesticated pets (e.g., cats, hamsters, mice, and guinea pigs). Treatment or diagnosis of humans is of particular interest.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs.

As used herein, the singular forms "a", "and", and "the" include plural referents unless the context clearly dictates otherwise. Thus, for example, reference to "a sample" also includes a plurality of such samples.

As used herein, an "algorithm" is a process that performs some sequence of operations to produce information.

Method for Measuring Differential Blood Oxygen Saturation

One aspect of the present invention provides a method for measuring differential blood oxygen saturation in a solid tumor in a subject. The method includes the steps of obtaining a first oxygenation image of a solid tumor before, during, or immediately after administration of vascular therapy to the subject; obtaining a second oxygenation image of the solid tumor after a devascularization time period; and determining a differential blood oxygen saturation value by comparing the first oxygenation image and the second oxygenation image. In some embodiments, the first oxygenation image and the second oxygenation image are converted to a first oxygenation value and a second oxygenation value before determining the differential blood oxygen saturation value. An algorithm can be used to convert the oxygenation images to oxygenation values.

Vascular therapy, as used herein, is any therapy that is used to treat a solid tumor by targeting the tumor vascular supply. Antiangiogenic therapies are vascular therapies that inhibit angiogenesis and interfere with new vessel formation. Vascular-disrupting approaches are other vascular therapies that target the established tumor blood vessels, resulting in tumor ischemia and necrosis are also vascular therapies. Tumors cannot grow to a size larger than 2 mm without angiogenesis, so vascular therapy is an effective means for treating and preventing the growth of solid tumors.

In some embodiments, the vascular therapy administered is photodynamic therapy. Photodynamic therapy involves the use of a photosensitizer, a light source and tissue oxygen. The combination of these three components leads to the chemical destruction of any tissues which have either selectively taken up the photosensitizer or have been locally exposed to light. The photosensitizer can be applied directly to the solid tumor, or can be allowed to preferentially accumulate in the solid tumor tissue. The wavelength of the light source needs to be appropriate for exciting the photosensitizer to produce reactive oxygen species. Examples of suitable photosensitizers include aminolevulinic acid (ALA), phthalocyanine compounds (e.g., Pc 4), m-tetrahydroxyphenylchlorin (mTHPC), mono-L-aspartyl chlorin e6 (NPe6), and benzoporphyrin.

In other embodiments, the vascular therapy administered is chemotherapy. Chemotherapeutic agents can include angiogenesis inhibitors and vascular disrupting agents. Examples of angiogenesis inhibitors include bevacizumab, itraconazole, carboxyamidotriazole, TNP-70, CM 101, IFN-α, IL-12, K1-3, DL-α-difluoromethyl-ornithine, fumagillin, genistein, minocycline, staurosporine, platelet factor 4, suramin, SU5416, thrombospondin, VEGFR antagonists, angiostatic steroids, cartilage-derived angiogenesis inhibitory factor, matrix metalloproteinase inhibitors, angiostatin, endostatin, 2-methoxyestradiol, tecogalan, tetrathiomolybdate, thalidomide, thrombospondin, prolactin, $\alpha v\beta 3$ inhibitors, linomide, tasquinimod, ranibizumab, sorafenib, sunitinib, pazobanib, everolimus, and cabozantinib (XL184). Vascular disrupting agents include microtubule destabilizing drugs such as combretastatin A-4 disodium phosphate (CA4P), ZD6126, AVE8062, and Oxi 4503, and other agents such as vadimezan and plinabulin.

In further embodiments, the vascular therapy administered is radiotherapy. Radiotherapy is known to cause vascular damage, and can be used either alone or in combination with vascular disrupting agents to provide vascular therapy of a solid tumor. See Park et al., Radiat Res., 177(3), p. 311-27 (2012), the disclosure of which is incorporated herein by reference.

Vascular therapy may consist of a single administration of a therapeutic agent. Vascular therapy may also comprise repeated administration over a period of time. Vascular therapy may also comprise a combination of two or more different vascular therapies that are either administered simultaneously or sequentially, where the differential blood oxygen saturation is determined for the combined effect of the two therapies. For example, photodynamic therapy may be combined with chemotherapy or radiotherapy, or two different chemotherapeutic agents and/or radiotherapeutic agents may be combined as the vascular therapy.

Blood (or tissue) oxygen saturation ($StO_2$), commonly referred to as "sats", measures the percentage of hemoglobin binding sites in the bloodstream occupied by oxygen. At low partial pressures of oxygen, most hemoglobin is deoxygenated. At around 90% (the value varies according to the clinical context) oxygen saturation increases according to an oxygen-hemoglobin dissociation curve and approaches 100% at partial oxygen pressures of >10 kPa. Levels of $StO_2$ below 90% are generally considered hypoxic. A differential blood oxygen saturation value, as used herein, refers to a change in blood oxygen saturation at a given location from one point in time to another. The step of determining a differential blood oxygen saturation value may evaluate the $StO_2$ level for a single location in the tumor or the tumor as a whole, or it may evaluate the $StO_2$ level for more than one location in the tumor. Accordingly, in some embodiments, the step of determining a differential blood oxygen saturation value comprises determining a plurality of differential blood oxygen saturation values from different locations in the first and second oxygenation images.

An oxygenation image, as used herein, is an image which provides information on the blood oxygen saturation within the tissue being imaged. The oxygenation image may be obtained through a variety of methods, and in particular through the use of non-invasive or minimally invasive imaging techniques. Examples of non-invasive techniques include photoacoustic imaging, magnetic resonance imaging (MRI), optical tomography, near-infrared spectroscopy such as near-infrared fluorescence (NIRF) imaging, or the like. In some embodiments the oxygenation image is obtained through photoacoustic imaging. This imaging modality is particularly useful in that it provides a three-dimensional image, has high resolution (approximately 200 μm for the mouse and 500 μm for human) and is commonly used by physicians to measure tumor volume. In further embodiments, the photoacoustic imaging can be combined with ultrasound imaging to characterize blood oxygen saturation values for one or more regions of the solid tumor.

In some embodiments, additional oxygenation images could be obtained for online dosimetry. For example three, four, five, six or more oxygenation images may be used in the methods as described herein. In some embodiments, in addition to the first and second oxygenation image, a third oxygenation image may be obtained during therapy for online (real-time) adjustment of treatment dosimetry parameters.

In some embodiments, the present invention provides systems (e.g., computer systems and/or software) that are configured to receive patient data related to tissue oxygenation levels, and optionally other patient data (e.g., additional tumor metabolic parameters) and to calculate and display the tissue blood oxygen saturation levels and/or a risk score. In some such embodiments, the system employs one or more algorithms to convert the oxygenation images and/or other biological data into a risk score. In some embodiments, the system comprises a database that associates tissue blood oxygen saturation levels with risk profiles, based, for example, on historic patient data, one or more control subjects, population averages, or the like. In some embodiments, the system comprises a user interface that permits a user to manage the nature of the information assessed and the manner in which the risk score is displayed. In some embodiments, the system comprises a display that displays a risk score to the user.

A devascularization time period is the length of time from the start of a vascular therapy until, if effective, devascularization has occurred in the solid tumor. The devascularization time period depends on the type of vascular therapy as well as the type of tumor. For example, for photodynamic therapy as measured in a mouse model, devascularization has occurred within 3 hours after beginning PDT therapy. Thus, in some embodiments, the preferred time frame for obtaining the second image is between 3 hours and 1 month, between three hours and one week, or more particular between 4 hours and two weeks, or between 6 hours and two weeks. While these time frames are calculated based on a mouse model, humans are expected to have a similar response.

For other therapies, devascularization may be slower or faster, dependent on the mechanism and the therapy. For example, some chemotherapeutics will take 2-4 days or more for devascularization. Bevacizumab (Avastin®) has a devascularization time of about 48-72 hours. For some other therapies, devascularization occurs after 30 minutes, 1 hour, 2 hours, 3 hours, 4 hours, 6 hours, 12 hours, after 24 hours, or more. In some embodiments, the devascularization time period can be pre-defined based on the type of therapy. Thus, measurement(s) after PDT therapy may be provided based on a set devascularization time of 2 hours, 3 hours, or 4 hours.

For some vascular therapies, the therapeutic agent is administered in several doses. Thus, for such therapies, the methods as described herein can be used for several purposes. For example, the effectiveness of a therapy in a particular patent can be analyzed after taking only a single dose (or several doses but less than the full therapeutic course). Thus, in this instance, the image taken after a devascularization time period is taken after devascularization based solely on the administration of a first dose. Using this devascularization time period is particularly useful, for example, in determining the effectiveness of the single dose, the effectiveness of the full course of therapy and whether it should be continued, or therapy probability of a cancer recurring after the completion of the vascular therapy. The look-up table used for such a method may be different from a look up table based on a full course of a vascular therapy, and may be determined for a particular therapeutic agent or may simply be calculated based on the expected result of administering the percent of a full dose, such as ⅓ or ¼ of the differential blood oxygen saturation level of a full dose. A look-up table is a set of pre-generated values were used to speed up calculations of complex functions. In data analysis applications, such as image processing, a lookup table (LUT) can be used to transform the input data into a more desirable output format. One common LUT, called the colormap or palette, is used to determine the colors and intensity values with which a particular image will be displayed.

In some embodiments where the therapeutic agent is administered in several doses, the methods described herein are performed only after the full course of therapy has been administered and the devascularization time period is the time for devascularization after the last dose of the therapeutic agent has been administered.

While it is important to wait until after devascularization before the second oxygenation image is obtained, there is no similar requirement to immediately image the tumor after devascularization. In fact, the image could be obtained 2 weeks, one month, or two months after devascularization. However, since tumor regrowth will begin to become evident via other indicators after a certain time period, the predictive and useful aspects of this technique decrease with time. For example, recurring U87 glioma tumors will become evident after about 25 days. However, other tumor types have much longer before their presence is evident. Thus, as a predictive tool is most relevant within 3 months, 1 month, or within 2 weeks, or even within 48 or 24 hours after devascularization. This time frame is dependent on the aggressiveness of the tumor or a tumor subpopulation, the type of vascular therapy and therapeutic dose, and the size of any tumor mass not devascularized.

In some embodiments, the method also includes determining one or more additional tumor metabolic parameters. Examples of tumor metabolic parameters include metabolic tumor volume (MTV), total lesion glycolysis (TLG), maximum standardized uptake value (SUVmax), mean SUV (SUVmean), and inverse coefficient of variation (1/CoV). Tumor metabolic parameters are often evaluated using [$^{18}$F] fluorodeoxyglucose-positron emission tomography/computed tomography.

In some embodiments, the solid tumor is contacted with one or more contrast agent before imaging. The contrast agents may be used to facilitate obtaining the first and or second oxygenation images, or they may be used in the determination of the one or more additional tumor metabolic parameters. The nature of the contrast agent will vary depending on the imaging technology being used, and the identity of appropriate contrast agents is known to those skilled in the art. In some embodiments, the one or more contrast agent is a molecular targeted contrast agent. Molecular targeted contrast agents are contrast agents that have been conjugated to antibodies or antibody fragments that specifically bind to cell surface ligands present on the solid tumor being evaluated using the method of the invention.

In some embodiments, the method also includes the step of comparing the differential blood oxygen saturation value to a blood oxygen saturation necrosis value. A blood oxygen necrosis value is an oxygen saturation value which is sufficiently low to cause necrosis of the tissue having that oxygen saturation value within a short period of time. The blood oxygen saturation necrosis value can vary depending on the particular tissue, and the exact amount of time allowed for necrosis to occur should that blood oxygen saturation value persist. The blood oxygen saturation necrosis value can be represented as an actual blood oxygen saturation value for the tissue, or alternately it can be represented as a percentage decrease from a typical blood oxygen saturation value. Examples of blood oxygen saturation necrosis values range from 0 to 40%, with a blood oxygen saturation necrosis value of 16% being representative for some types of solid tumor tissue. Alternately, a blood oxygen saturation necrosis value can represent a decrease in blood oxygen saturation from about 70% to about 100%, with a decrease in blood oxygen saturation of about decrease of about 80% being typical for successfully treated solid tumor tissue. In some embodiments, the blood oxygen saturation necrosis value used in the method is obtained from a look-up table.

In some embodiments, the step of determining a differential blood oxygen saturation value further comprises spatially co-registering the first oxygenation image with second oxygenation image; forming a differential image including a plurality of differential blood oxygen saturation values by comparing a plurality of regions of the first oxygenation image and the second oxygenation image. Co-registration refers to overlaying structural and functional images to link functional scans with an anatomical scan. The plurality of differential blood oxygen saturation values can then be used to generate a treatment map by comparing the plurality of differential blood oxygen saturation values in the differential image to the blood oxygen saturation necrosis value. Region(s) of the solid tumor corresponding to regions of the images having blood oxygen saturation levels less than the blood oxygen saturation necrosis value are then defined as responder region(s), while region(s) of the solid tumor corresponding to regions of the images having blood oxygen saturation level more than the blood oxygen saturation necrosis value are defined as potential regrowth region(s). The treatment map can be used to indicate which regions of a solid tumor have been successfully treated, and which, if any, or the regions of the tumor may exhibit recurrence of the tumor after therapy.

One aspect of the invention provides a method for providing a prognosis of tumor recurrence in a patient, comprising obtaining a first oxygenation image of a solid tumor before, during, or immediately after administration of vascular therapy to the patient; obtaining a second oxygenation image of the solid tumor after a devascularization time period; determining a differential blood oxygen saturation value by comparing the first oxygenation image and the second oxygenation image; comparing the differential blood oxygen saturation value to a blood oxygen saturation necrosis value; and providing a prognosis for tumor recurrence in the patient if the differential blood oxygen saturation value is higher than the blood oxygen saturation necrosis value.

Another aspect of the invention provides method of treating a patient having a solid tumor, comprising: obtaining a first oxygenation image of a solid tumor before, during, or immediately after administration of vascular therapy; obtaining a second oxygenation image of the solid tumor after a devascularization time period; determining a differential blood oxygen saturation value by comparing the first oxygenation image and the second oxygenation image; comparing the differential blood oxygen saturation value to a blood oxygen saturation necrosis value; and providing antitumor therapy to the patient if the differential blood oxygen saturation value is higher than the blood oxygen saturation necrosis value.

A further aspect of the invention provides a method of determining the effectiveness of a vascular therapy for a patient having a solid tumor, comprising: obtaining a first oxygenation image of a solid tumor before, during, or immediately after administration of vascular therapy; obtaining a second oxygenation image of the solid tumor after a devascularization time period; spatially co-registering the first oxygenation image with the second oxygenation image; forming a differential image including a plurality of differential blood oxygen saturation values by comparing a plurality of regions of the first oxygenation image with a corresponding plurality of regions of the second oxygenation image; comparing the plurality of differential blood oxygen saturation values in the differential image to a blood oxygen saturation necrosis value; defining region(s) of the solid tumor corresponding to regions of the images having blood oxygen saturation levels less than the blood oxygen saturation necrosis value as responder region(s); defining region(s) of the solid tumor corresponding to regions of the images having blood oxygen saturation level more than the blood oxygen saturation necrosis value as potential regrowth region(s); and characterizing the vascular therapy as effective where there are no potential regrowth region(s), or any potential regrowth regions have only small differences between the blood oxygen saturation levels greater than the blood oxygen saturation necrosis value. For example, regions of the images having a blood oxygen saturation level of 16% or less can be defined as responder regions.

Solid Tumors

As used herein, the terms "tumor" or "cancer" refer to a condition characterized by anomalous rapid proliferation of abnormal cells of a subject. The abnormal cells often are referred to as "neoplastic cells," which are transformed cells that can form a solid tumor. The term "tumor" refers to an abnormal mass or population of cells (e.g., two or more cells) that result from excessive or abnormal cell division, whether malignant or benign, and pre-cancerous and cancerous cells. Malignant tumors are distinguished from benign growths or tumors in that, in addition to uncontrolled cellular proliferation, they can invade surrounding tissues and can metastasize.

A solid tumor is a malignancy that forms a discrete tumor mass of tissue that usually does not contain cysts or liquid areas. It may be any tumor of the tissue such as a sarcoma, a carcinoma, or a lymphoma. Different types of solid tumors are named for the type of cells that form them. For example, a solid tumor can be a bladder, brain, breast, prostate, lung, liver, ovarian, testicular, colorectum, or kidney tumor; or sarcoma or melanoma. In one embodiment, wherein the oxygenation image is obtained through photoacoustic imaging, the solid tumor is a solid tumor located in a tissue other than the lung. In some embodiments, the solid tumor is a glioma (i.e., a tumor forming in the brain or spine) or a solid tumor resulting from pancreatic cancer.

The presence of a solid tumor can be confirmed using a variety of techniques known to those skilled in the art. Examples of procedures suitable for determining whether a subject has a solid tumor include, but are not limited to, digital examination, cystoscopy, ultrasound, infrared spectral analysis, and magnetic resonance imaging. A preferred method for confirming the presence of a solid tumor is to obtain a biopsy. In a biopsy, a tissue sample is typically obtained from a suspect tissue region using a biopsy gun which inserts and removes special hollow-core needles. The tissue samples are then examined under a microscope to determine whether cancer cells are present, and to evaluate the microscopic features of any cancer found to further characterize and possible stage the cancer.

Antitumor Therapy

In some embodiments, subjecting having solid tumors identified as having a high risk of recurrence may be treated with antitumor therapy. Antitumor therapy can include any of the vascular therapy techniques already described herein. In addition, antitumor therapy can include ablating the cancer using a method selected from the group consisting of cryoablation, thermal ablation, radiotherapy, chemotherapy, radiofrequency ablation, electroporation, alcohol ablation, high intensity focused ultrasound, photodynamic therapy, administration of suitable monoclonal antibodies, and administration of immunotoxins.

In some embodiments, antitumor therapy includes administering a therapeutically effective amount of an anticancer agent to the subject. There are a wide variety of anticancer agents that have an effect other than angiogenesis inhibition or vascular disruprtion. Examples of anticancer agents include DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-α, rapamycin, thapsigargin, and bikunin, and derivatives (as defined for imaging agents) thereof.

FIG. 1 is a flow diagram illustrating a method for treating a solid tumor in accordance with an aspect of the present invention. Once the patient is diagnosed with a solid tumor, pretreatment imaging can be performed to determine one or more characteristics of the tumor. For example, it can be determined if the tumor is hypoxic or non-hypoxic. Once the tumor has been characterized, a treatment specific to tumors having the determined characteristics can be administered.

Post-treatment imaging is performed after an appropriate period of time for evaluating the effectiveness of the treatment. This time can be dependent on the characteristics of the tumor and biometric parameters of the patient, such as age, medical history, sex, etc., and the specific time can be determined from a look-up table or database. Once the post-treatment imaging has been performed, a prediction map can be made comparing the two images to determine which portions of the tumor have responded to therapy. If the tumor has been successfully treated, the method terminates. Otherwise, the method returns to the initial step to renew the treatment process.

Figure 2:
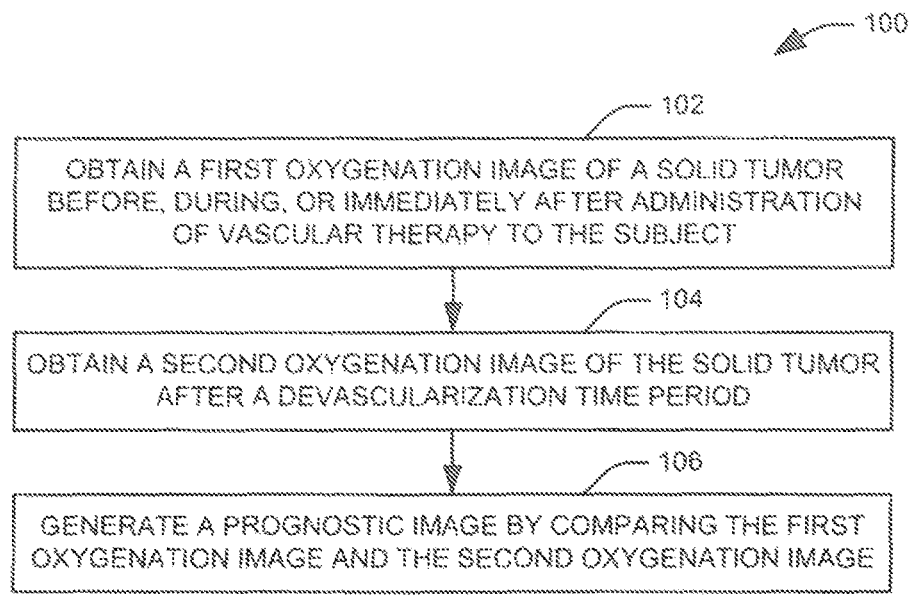
FIG. 2 illustrates an example method for determining the effectiveness of vascular therapy for a patient having a solid tumor in accordance with an aspect of the present invention.

FIG. 2 illustrates an example method 100 for determining the effectiveness of vascular therapy for a patient having a solid tumor in accordance with an aspect of the present invention. At 102, a first oxygenation image of a solid tumor is obtained before, during, or immediately after administration of vascular therapy to the subject. At 104, a second oxygenation image of the solid tumor is obtained after a devascularization time period. At 106, a prognostic image, providing a visual representation of the effectiveness of the vascular therapy, is generated by comparing the first oxygenation image and the second oxygenation image.

Computer Processing of Images

Figure 3:
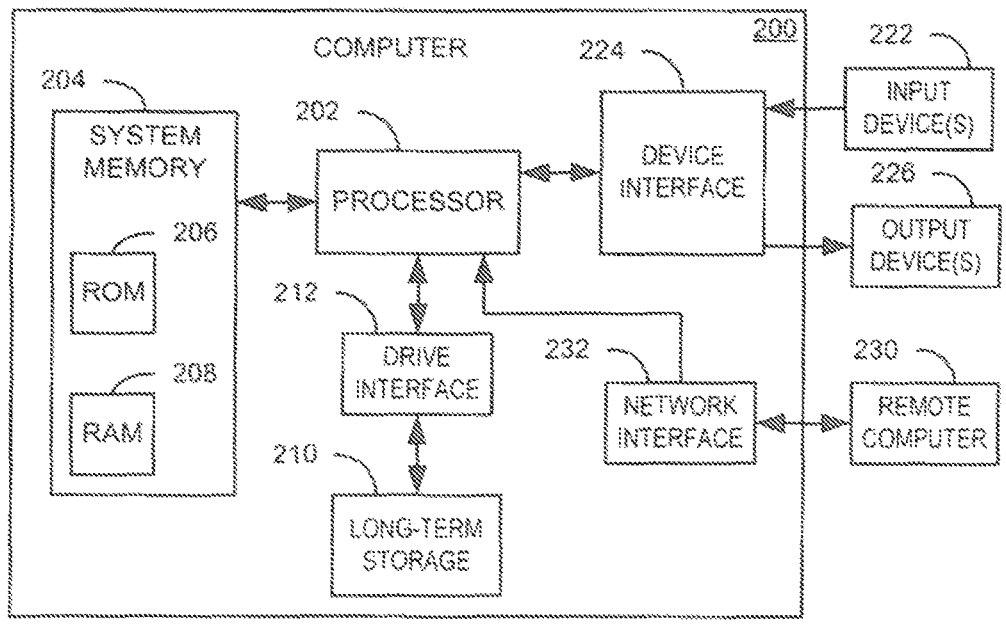
FIG. 3 illustrates an example method for providing a prognostic image, in accordance with an aspect of the present invention.

FIG. 3 illustrates an example method 150 for providing a prognostic image, in accordance with an aspect of the present invention. In the illustrated example, the method 150 is performed via a computer software system that includes a non-transitory computer-readable medium on which program instructions are stored and a data processor that executes the instructions to provide the prognostic image. It will be appreciated, however, that the illustrated method could be instead performed by dedicated hardware or a combination of dedicated hardware and a general purpose computer executing software instructions.

At 152, at least two three-dimensional oxygenation images of a solid tumor are received at the system. In one example, the images are provided from an associated photoacoustic imaging system. At 154, the images are registered to create a differential image comprising the difference in blood oxygen saturation between the images. For example, a spatial registration can be performed on the images via any appropriate method, and the differential image can be produced as a voxel-by-voxel subtraction of the oxygenation values of the second image from the oxygenation values of the first image. It will be appreciated that the spatial registration measure can be performed by any appropriate registration algorithm. In one implementation, the registration can be performed by finding an alignment of the two images providing an optimal value for a similarity measure between the two images.

At 156, a database storing a blood oxygen saturation necrosis value is accessed. It will be appreciated that the database could contain a plurality of blood oxygen saturation necrosis values, with an appropriate value selected according to a tissue in which the tumor appears, a type and stage of the tumor, and one or more biometric parameters of the patient. At 158, the prognostic image is created such that portions of the solid tumor having a differential blood oxygen saturation greater than the blood oxygen saturation necrosis value are visually distinguished from portions of the solid tumor having a differential blood oxygen saturation less than the blood oxygen saturation necrosis value. Accordingly, those portions of the tumor for which the vascular therapy has been effective can be quickly identified by a medical professional.

Figure 4:
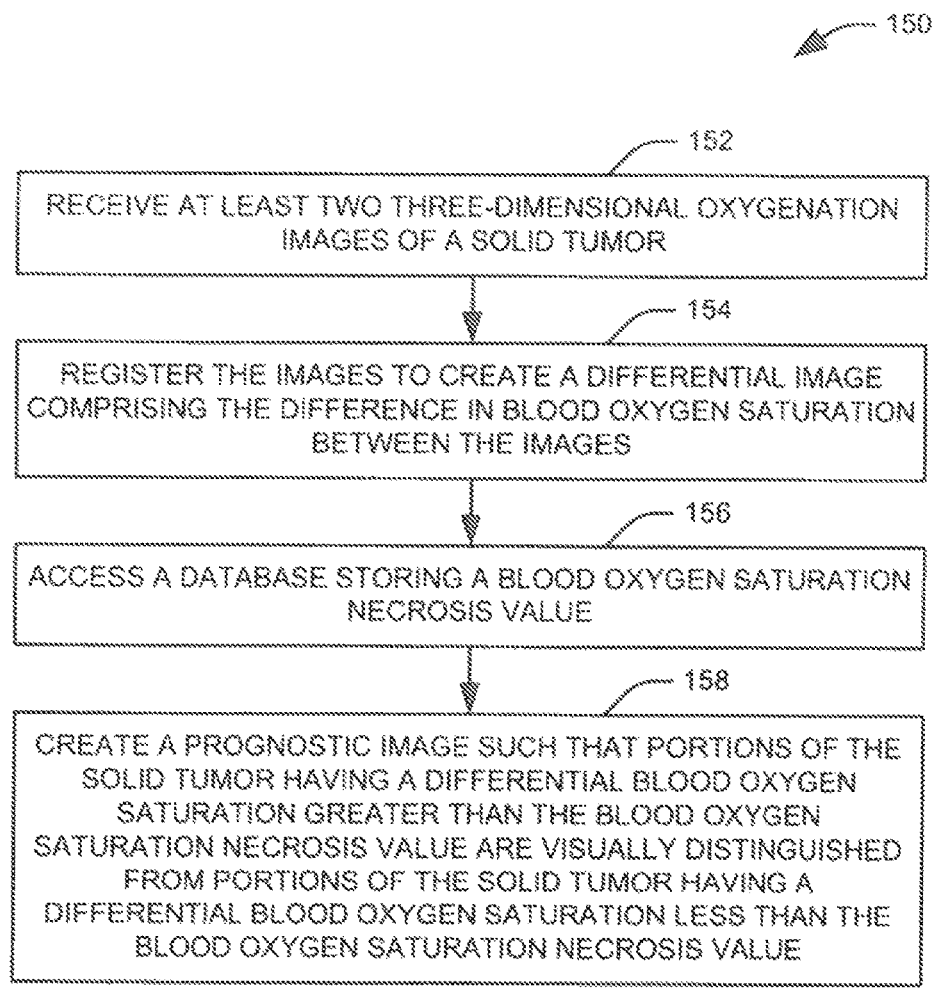
FIG. 4 illustrates a computer system 200 that can be employed to implement systems and methods described herein.

FIG. 4 illustrates a computer system 200 that can be employed to implement systems and methods described herein, such as based on computer executable instructions running on the computer system. The computer system 200 can be implemented on one or more general purpose networked computer systems, embedded computer systems, routers, switches, server devices, client devices, various intermediate devices/nodes and/or stand alone computer systems.

The computer system 200 includes a processor 202 and a system memory 204. Dual microprocessors and other multi-processor architectures can also be utilized as the processor 202. The processor 202 and system memory 204 can be coupled by any of several types of bus structures, including a memory bus or memory controller, a peripheral bus, and a local bus using any of a variety of bus architectures. The system memory 204 includes read only memory (ROM) 206 and random access memory (RAM) 208. A basic input/output system (BIOS) can reside in the ROM 206, generally containing the basic routines that help to transfer information between elements within the computer system 200, such as a reset or power-up.

The computer system 200 can include one or more types of long-term data storage 210, including a hard disk drive, a magnetic disk drive, (e.g., to read from or write to a removable disk), and an optical disk drive, (e.g., for reading a CD-ROM or DVD disk or to read from or write to other optical media). The long-term data storage 210 can be connected to the processor 202 by a drive interface 212. The long-term data storage 210 components provide nonvolatile storage of data, data structures, and computer-executable instructions for the computer system 200. A number of program modules may also be stored in one or more of the drives as well as in the RAM 208, including an operating system, one or more application programs, other program modules, and program data.

A user may enter commands and information into the computer system 200 through one or more input devices 222, such as a keyboard or a pointing device (e.g., a mouse). These and other input devices are often connected to the processor 202 through a device interface 224. For example, the input devices can be connected to the system bus by one or more a parallel port, a serial port or a universal serial bus (USB). One or more output device(s) 226, such as a visual display device or printer, can also be connected to the processor 202 via the device interface 224.

The computer system 200 may operate in a networked environment using logical connections (e.g., a local area network (LAN) or wide area network (WAN) to one or more remote computers 230. A given remote computer 230 may be a workstation, a computer system, a router, a peer device or other common network node, and typically includes many or all of the elements described relative to the computer system 200. The computer system 200 can communicate with the remote computers 230 via a network interface 232, such as a wired or wireless network interface card or modem. In a networked environment, application programs and program data depicted relative to the computer system 200, or portions thereof, may be stored in memory associated with the remote computers 230.

Examples have been included to more clearly describe a particular embodiment of the invention and its associated cost and operational advantages. However, there are a wide variety of other embodiments within the scope of the present invention, which should not be limited to the particular examples provided herein.

EXAMPLES

Figure 5:
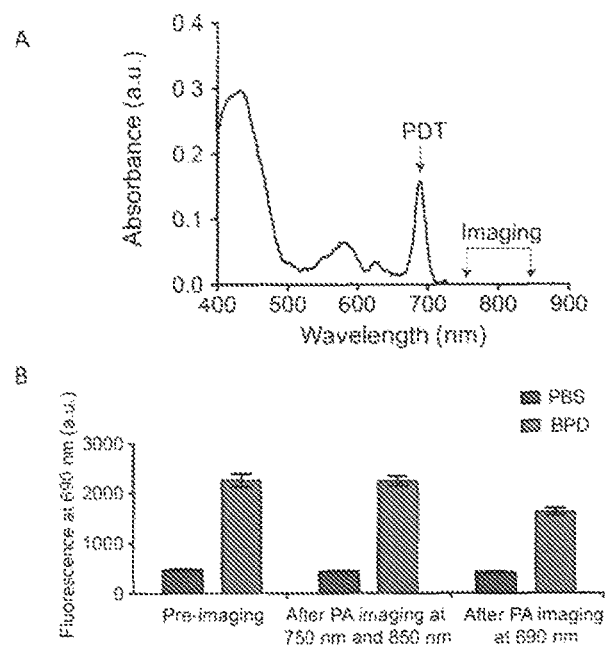
FIG. 5 provides graphs showing that photoacoustic imaging for $StO_2$ does not photobleach the photosensitizer. A. Optical absorption properties of the photosensitizer BPD. PDT was performed at 690 nm and PAI was performed at 750 and 850 nm wavelength illumination. (B) Fluorescence from tubes containing PBS or BPD before and after PAI at 750 nm, 850 nm and after PAI at 690 nm. There is no significant difference between the BPD fluorescence (no photobleaching) before and after PAI at 750 nm and 850 nm. However, PAI at 690 nm photobleached the BPD, causing a significant decrease in the fluorescence.
Figure 6:
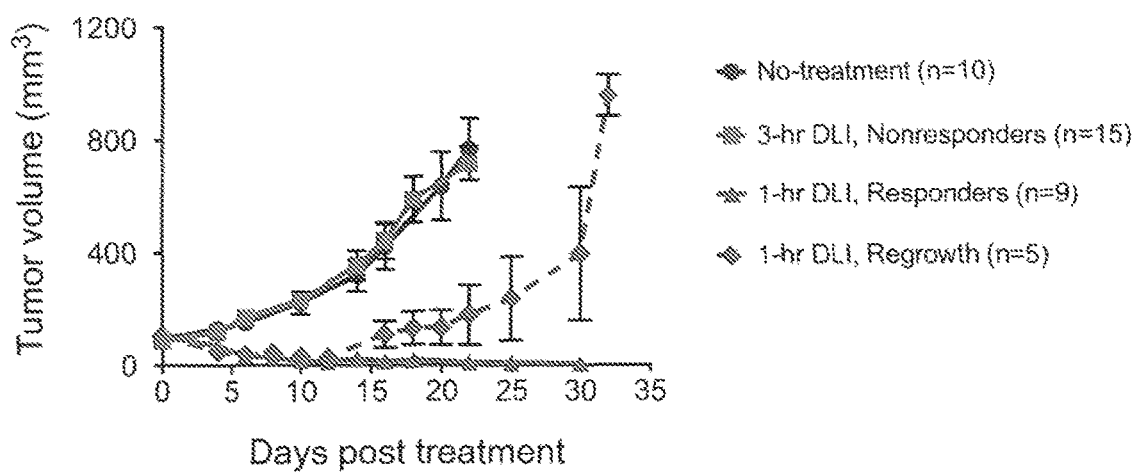
FIG. 6 provides a graph showing longitudinal volume monitoring of subcutaneous U87 tumors that underwent no-treatment (circles), BPD-PDT with 3-hr DLI (squares), BPD-PDT with 1-hr DLI showing complete response (triangles) and BPD-PDT treatment with 1-hr DLI showing regrowth (diamonds). The error bars indicate SEM.

Example 1: Prediction of Tumor Recurrence and Therapy Monitoring Using Ultrasound-Guided Photoacoustic Imaging It was hypothesized that mapping the change in $StO_2$, a surrogate marker for oxygen consumption, within the 3D tumor volume could predict the likelihood of PDT success and could identify regions of local tumor recurrence within the 3D tumor volume. The inventors tested this hypothesis by using, for the first time, PAI monitoring of Benzoporphyrin-derivative (BPD) based PDT-induced change in tumor $StO_2$ in a murine model of GBM. It was demonstrated that a ~95% and ~85% decrease in $StO_2$ at 6 and 24-hrs post-therapy respectively were predictive of tumors responding to the treatment (i.e., no palpable tumor was observed up to a month post therapy) while no significant change in $StO_2$ at post-therapy was observed in the non-responding tumors. Based on these findings, a "prediction map" was deduced from the PAI $StO_2$ images post-therapy to predict non-treated and regrowth areas with the 3D volume of the tumor. Finally the prediction map was validated with blinded caliper measurements and photographs of the recurred tumor.
Results
Photoacoustic Imaging for $StO_2$ does not Photobleach Photosensitizer The FDA approved photosensitizer Benzoporphryin derivative (BPD-MA) (Aveline et al., Photochemistry and Photobiology, 59(3):328-35 (1994)) with absorption peaks at 405 nm (Q-band) and 690 nm (Soret band) was used for all PDT experiments. To achieve better depth of light penetration, 690 nm light was used for PDT. PAI was performed at 750 nm and 850 nm wavelength illumination to deduce $StO_2$ from the oxygenated and deoxygenated hemoglobin signal as described by Needles et al. Needles et al., IEEE Trans Ultrason Ferroelectr Freq Control. 60(5):888-97 (2013). At these wavelengths, the absorbance of BPD is minimal (FIG. 5A). PAI was performed using pulsed nanosecond laser (10 nsec pulse width) illumination. PAI on phantom tubes (approximately 500 µm inner diameter) loaded with BPD helped gauge the photobleaching effects that might emanate from the measurement due to the pulsed nanosecond laser irradiation. Fluorescence imaging on the tubes were performed using a Maestro imaging system (CRI Inc.) with an excitation at 405 nm and emission at 690 nm. Fluorescence from the tubes at 690 nm prior to PAI and post PAI imaging is displayed in FIG. 5B. There was no significant change in the fluorescence signal in the tube compared to pre-imaging value with PAI at 750 nm followed by 850 nm irradiation. However, reduced fluorescence was observed in the tubes post PAI at 690 nm due to photobleaching effects on BPD at this wavelength. Overall these results indicate PAI for $StO_2$ has minimal photobleaching effect on BPD and no PDT effects occurring due to the imaging procedure.
Effect of Drug-Light-Interval (DLI) on PDT Treatment Response The inventors' previous studies established that PDT was more effective when light is initiated 1-hr post I.V. injection of PS (1-hr drug-light-interval, DLI) compared to 3-hr DLI. Chen et al., Int J Radiat Oncol Biol Phys., 61(4):1216-26 (2005); Chen et al., Crit Rev Eukaryot Gene Expr., 16(4):279-305 (2006). It was postulated in previous work that at 1-hr the PS localizes to both cellular and vascular compartments of the tumor while at 3-hrs, most of the PS is extra vascular and primarily cellular therefore less likely to impact the tumor oxygenation status. Iinuma et al., Cancer Research, 59(24):6164-70 (1999). Identical results were obtained in the U87 glioma model in the current study as shown in FIG. 6. The 3-hr DLI group tumors showed approximately six-fold increase in volume at three weeks following PDT. There was no significant difference (p>0.05, Students t-test) between the no-treatment group and the 3-hr DLI group. Amongst the mice that underwent PDT with 1-hr DLI, there was no regrowth for ~two weeks and at that point 35% of the mice started to show recurrence and an increase in tumor volume (FIG. 6, dashed line), while 65% mice had no palpable tumor 30 days post therapy (FIG. 6, solid line). To test if PAI could monitor the changes in $StO_2$ in the tumor due to PDT, The inventors designated the 1-hr DLI group with a sustained absence of palpable tumors up to 30 days post treatment (FIG. 6, triangles joined by solid line) as the "PDT responding group" and the mice in the 3-hr DLI group (FIG. 6, squares joined by solid line) were considered the "PDT non-responding group".
Pre-PDT and Immediate Post-PDT $StO_2$ and HbT Values do not Predict Treatment Response.

Figure 7:
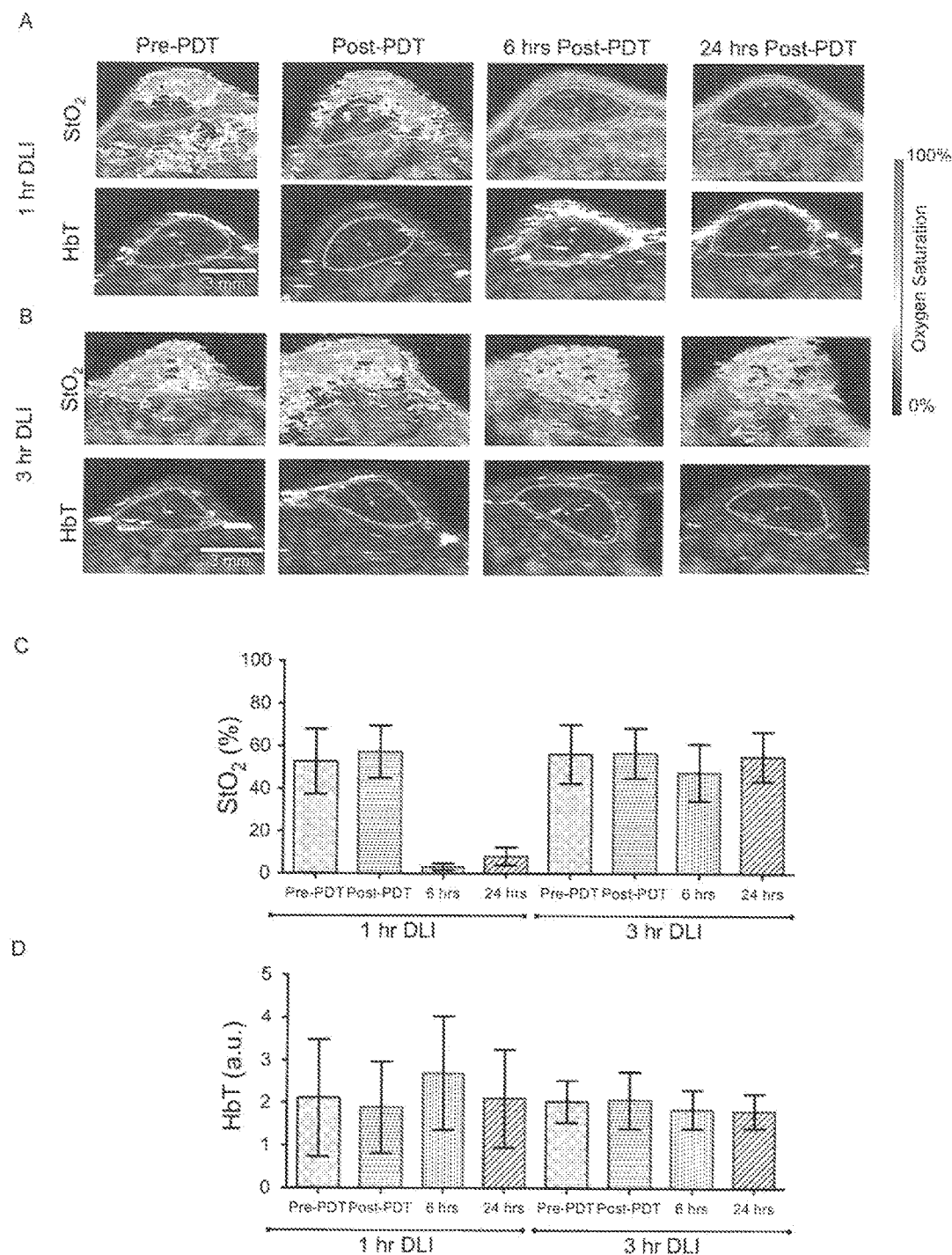
FIG. 7A-D provides images and bar graphs. The top panels (A&B) represents ultrasound image overlaid with oxygen saturation map where blue and red represent hypoxic and oxygenated regions, respectively. The ROI indicates the tumor region identified using ultrasound image. The bottom panels (C&D) show mean $StO_2$ and HbT values at various time points (Pre-PDT, Post-PDT, 6-hrs and 24-hrs post-PDT) in the 1-hr DLI and 3-hr DLI groups. Error bars indicate standard deviation.

$StO_2$ and HbT content were measured in both the 1-hr DLI responding group and 3-hr DLI (nonresponders) group of mice (n=6 per group) at 4 time points (before PDT (Pre-PDT), immediately post-PDT, 6-hrs and 24-hrs post-PDT) to determine if PAI could predict treatment response. FIG. 7A and FIG. 7B show representative images of the change in $StO_2$ and HbT content at various time points in a responding and non-responding tumor respectively. Ultrasound imaging identified region of interest (green ROI in FIGS. 7A and 7B is the tumor region). FIG. 7C and FIG. 7D represent the average of $StO_2$ values and HbT values in the tumor ROI from ~350 B-scans per mouse (6 mice in each group, ~55-75 B-scans per 3D tumor volume). Prior to PDT, there was no statistically significant difference between the $StO_2$ of the 1-hr DLI and 3-hr DLI groups. There was no statistically significant difference between the pre-PDT and post-PDT values in the 3-hr DLI group, however the difference was significant (p<0.001) in the 1-hr DLI group, indicating an increase in oxygenation immediately post-PDT. This phenomena is in agreement with the studies by Wang et al. and is attributed to cell death and a decrease in the metabolic consumption of oxygen in the tumor area. Wang et al., Cancer Research, 64(20):7553-61 (2004). No significant difference in the post-PDT $StO_2$ was observed between the 1-hr and 3-hr DLI groups. These results are in agreement with Wang et al. who utilized broad band reflectance spectroscopy to evaluate $StO_2$ in the PDT responders and control tumors. The inventors also observed no statistically significant difference between the total hemoglobin (HbT) values of the 1-hr DLI and 3-hr DLI groups prior to PDT. Furthermore, there was no statistically significant difference between the pre-PDT and post-PDT values in these groups amongst themselves or compared to their respective pre-PDT values. Indeed, the photoacoustic images also do not show any observable changes in the HbT images (FIGS. 7A and 7B). Based on these results, the pre-PDT $StO_2$ and HbT values and the immediately post-PDT $StO_2$ and HbT values cannot by themselves be reliably used to predict PDT treatment response and differentiate the 1-hr and 3-hr DLI groups.

Six and 24-Hrs Post-PDT $StO_2$ Values Predict Treatment Response

The $StO_2$ values decreased in the responding 1-hr DLI group 6-hrs post-PDT to 2.9%±1.6% (~94.3% lower than Pre-PDT $StO_2$ value) i.e., the tumor has become hypoxic due to PDT induced vasoconstriction that is consistent with prior reports. Osaki et al., Cancer Letters, 248(1):47-57 (2007); Becker et al., Biomed Opt Express. 2(1):123-30 (2011); Chen et al., Radiat. Res.; 160(4):452-9 (2003). At 24-hrs post treatment, the $StO_2$ in the tumors was 8.03%±4.13% (~84.8% lower than its pre-PDT value compared to the 94% at 6-hrs post therapy). A statistically significant increase in average $StO_2$ was observed at 24-hrs post-PDT compared to values at 6-hrs post-PDT. In the non-responding 3-hr DLI group, $StO_2$ values were 47.6%±13.4% and 55.3%±11.6% at 6-hrs and 24-hrs post-PDT respectively. No statistically significant difference was observed between the pre-PDT values and 24-hrs post-PDT $StO_2$ values in the 3-hr DLI group. The decrease in $StO_2$ at 6-hrs in the 3-hr DLI group is statistically significant when compared to pre-PDT $StO_2$ value (~18% change) and could be due to PDT action with available BPD not cleared from the tumor at this time point. Indeed, a study by Osaki et al. and Chen et al showed less disruption of vasculature and therefore less change in $StO_2$ due to 3-hr DLI BPD-PDT.

The $StO_2$ maps by PAI clearly show hypoxic areas at both 6 and 24-hrs in the 1-hr DLI group (FIG. 7A). Interestingly, the HbT value at 6-hrs is significantly higher than the pre-PDT value in the 1-hr DLI group. The increase in HbT in the responders can be attributed to erythema caused by PDT. Mallidi et al., J. Biomed. Opt., 19(2):028001 (2014). The inflammation response due to PDT recruits additional red blood cells into the tumor region causing an increase in the HbT signal. There was no statistical difference in the HbT signal at 6-hrs and 24-hrs post-PDT in the 3-hr DLI group. Overall, PAI performed at 6-hrs and 24-hrs post-PDT was predictive of PDT treatment response and differentiated between the responding 1-hr DLI group and non-responding 3-hr DLI group based on the $StO_2$ values. Receiver-operating-curve analysis on the two parameters $StO_2$ at 6-hrs and $StO_2$ at 24-hrs suggested no significant difference in their treatment success predictive capability.

Validation of Tumor Hypoxia with Immunofluorescence

Figure 8:
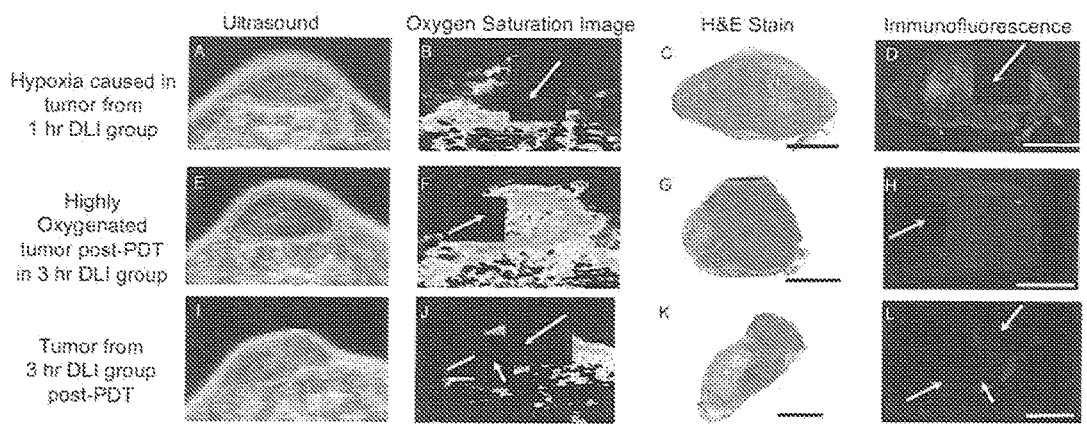
FIG. 8 provides images showing the validation of hypoxic conditions observed in photoacoustic images with immunofluorescence. Ultrasound, Oxygen saturation photoacoustic image, H&E and immunofluorescence image of a representative tumor cross-section is shown from the 1-hr DLI group (A-D), highly oxygenated tumor from the 3-hr DLI group (E-H) and tumor with few hypoxic regions in the 3-hr DLI group (I-L). White arrows indicate hypoxic areas. CD31 stain depicting tumor microvasculature is shown and pimonidazole stain indicating hypoxia is also shown in the immunofluorescence images. Arrows also indicate hypovascular area. Due to hypo-vascularity, no signal is observed in the photoacoustic image. The scale bar on the ultrasound and photoacoustic image represents 5 mm and the black and white scale bars on the H&E and immunofluorescence images respectively represents 1 mm.

The inventors next validated the hypoxic conditions observed in photoacoustic images with pimonidazole stain for hypoxia. Gerling et al., Theranostics, 4(6):604-13 (2014). Tumors were sectioned in a similar orientation as the imaging cross-section. CD31 stain was utilized to depict the tumor vasculature while pimonidazole stained the hypoxic regions. In the 1-hr DLI group (FIGS. 8A-4D), Immunofluorescence (IF) images show hypoxia adjacent to the vasculature depicted by the CD31 stain. The hypoxia is due to the vascular damage caused by PDT and disruption of the blood flow in these vessels. Zoomed images of the H&E stain of the adjacent cross section show vascular congestions. This phenomena of vascular disruption due to PDT agrees with previous study by Geel et al. (van Geel et al., British Journal of Cancer, 73(3):288-93 (1996)) and the presence of vascular congestion in tumors that responded to PDT treatment agrees with study by Maas et al. Maas et al., Cancer Research, 72(8):2079-88 (2012). Moreover, Busch et al. have shown that PDT can create significant hypoxia in tissue adjacent to perfused blood vessels. Busch et al., Cancer Research, 62(24):7273-9 (2002) The oxygen saturation maps by PAI clearly show a hypoxic region (FIG. 8B, top left region of the tumor shown by white arrow) in the areas where high pimonidazole stain was observed (FIG. 8D, top left region of the tumor shown by white arrow). Sections from two different tumors in the 3-hr DLI group are shown in the center and bottom panel of FIG. 8. In the center panel, the tumor is highly oxygenated and hence no pimonidazole stain was observed in this tumor section (FIG. 8H). The PAI image (FIG. 8F) also shows a highly oxygenated tumor. The grey arrow in FIG. 8F and FIG. 8H points to a non-vascular region within the tumor where PAI lacks contrast due to lack of blood vessels in this region. A similar hypo-vascular region was observed in bottom panel tumor (FIG. 8J and FIG. 8L, grey arrows) as well. These hypo-vascular areas existed prior to PDT as shown by PAI. The tumor in bottom panel has a few hypoxic regions (FIG. 8J and FIG. 8L, white arrows) and the hypoxia pattern correlated with the PAI. It is not unusual to tumors of 5-8 mm diameter to possess hypoxia region due to necrosis. It is also to be noted that the fluorescence of the pimonidazole stain is stronger in the 1-hr DLI (responding group) tumor than in the 3-hr DLI (non-responding) group given the severe hypoxic conditions created by PDT.

Tumor Regrowth Prediction with 6-Hr Post-PDT and 24-Hr Post-PDT $StO_2$ Values.

Figure 9:
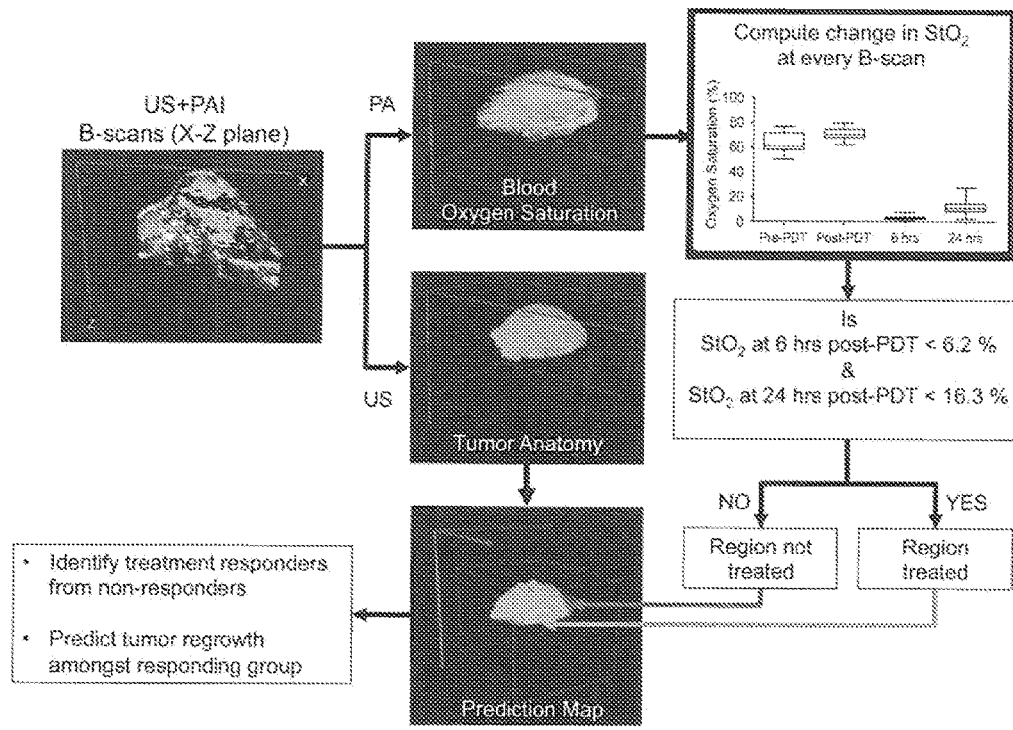
FIG. 9 provides a schematic algorithm to obtain PDT treatment prediction map from the ultrasound (US) and photoacoustic (PA) images for identifying treatment responders from nonresponders and for prediction of tumor regrowth.

Within the 1-hr DLI responding group, it was noticed that ~35% tumors had local recurrence (FIG. 6, dashed line) while the rest of the mice showed no visible or measurable tumor mass 30 days post treatment. Mice with recurrent tumors showed regrowth post-treatment after an initial decrease in tumor volume up to ~two weeks post treatment. The results in FIG. 7 suggests that the $StO_2$ reduced to 2.97±1.6% 6-hrs post-PDT and 8.03%±4.13% 24-hrs post-PDT in tumors that responded to treatment. Based on these results, the inventors devised an algorithm to analyze the $StO_2$ images of the recurrent tumors obtained at various time points post therapy. First, ultrasound and photoacoustic image B-scans were acquired at 0.152 mm step size to obtain 3D map of the anatomy and $StO_2$ respectively. At every B-scan, the tumor region was mapped using ultrasound image and the average $StO_2$ in the region was calculated. If the average $StO_2$ at 6-hrs post-PDT and 24-hrs post-PDT at the particular B-scan frame was less than 6.2% and 16.3%, (mean+2×standard deviation to include 95% of the data obtained from the responding group) the B-scan region was considered treated and pseudo-colored as green, else the regions were pseudo-colored red to indicate no treatment (FIG. 9). The algorithm is repeated for all the B-scans in the 3D tumor volume. This methodology will aid us in identifying treatment responders from nonresponders and also aid in predicting the regions of the tumor that did not receive complete treatment and could have the potential to regrow.

Figure 10:
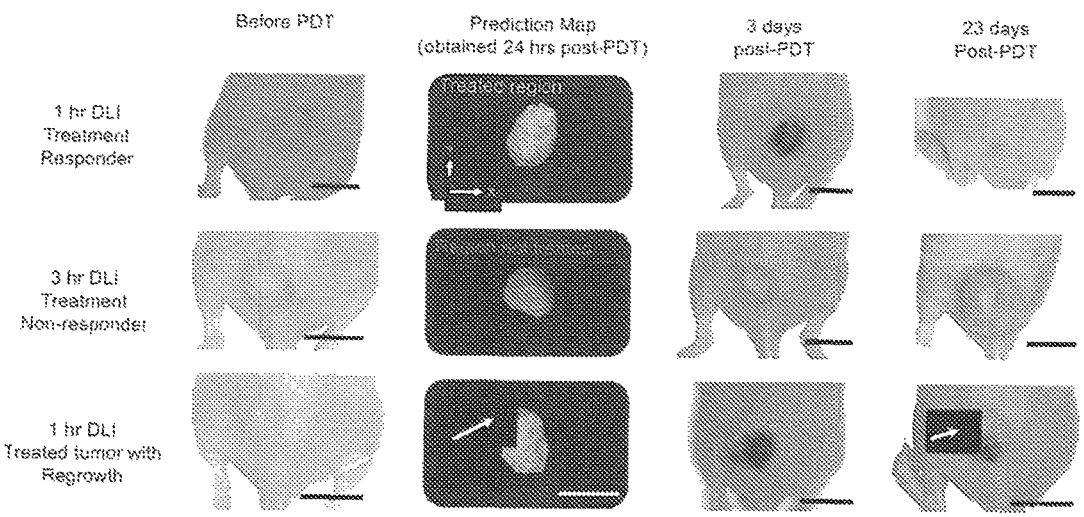
FIG. 10 provides images showing a tumors and a treatment prediction map calculated 24-hrs post-PDT from photoacoustic $StO_2$ maps in three different groups. Photographs of the same tumor are shown at different time points: before PDT, 3 days post treatment and 23 days post treatment. The scale bars in the photographs represent 1 cm. One region in the prediction map indicates treated regions and the other areas represent non-treated regions. Top panel represents mouse in the 1-hr DLI group (treatment responders) that showed no visible tumor regrowth at 23 days post-PDT. Center panel shows a mouse in the 3-hr DLI group. This mouse did not show any necrosis at 3 days posttreatment and continued to grow. The prediction map clearly shows that this tumor was not treated. Bottom panel shows a representative mouse in the 1-hr DLI group that had tumor regrowth. 3 days post therapy the tumor appeared to have complete necrosis however prediction map indicated a non-treated region in the top half of the tumor (indicated by white arrow). 23 days post therapy one can observe regrowth from the same region of the tumor as shown by the prediction map.

FIG. 10 shows representative photographs of subcutaneous tumors at various time points post-treatment and their respective "prediction" map. The photographs of the 1-hr DLI responding group showed bluish black necrosis of the tumor within 3 days post PDT and no visible or palpable signs of tumor 23 days post-PDT. The treatment prediction algorithm yielded "green"—color tumor region indicating that the tumor was completely treated and the $StO_2$ values in the tumor were below 6.2% and 16.3% at 6-hrs and 24-hrs post-PDT. The 3-hr DLI non-responding tumor showed no visible signs of damage 3 days post-PDT and the tumor volume continued to increase. The map yielded a "red"-color tumor indicating the tumor was not treated. In the case of tumor that had regrowth (FIG. 10, bottom panel), 3 days post treatment, the complete tumor appeared to be necrosed and visibly no tumor was observable until 18 days post treatment. Measurable tumor was observed only around day 20 post-treatment. The prediction map showed that the region of this tumor (indicated by white arrow) did not have sufficient decrease in $StO_2$ to cause complete tumor necrosis. These results suggest that the oxygen saturation levels need to decrease significantly post-PDT and sustain these hypoxic conditions for a period of 24-hrs posttreatment for complete tumor necrosis.

Figure 11:
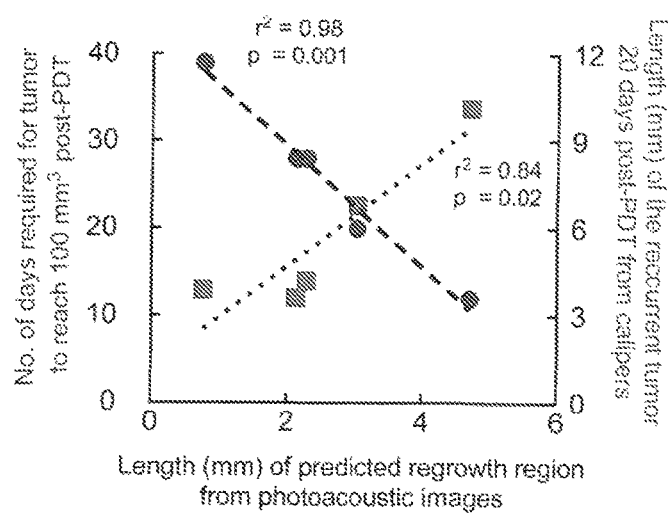
FIG. 11 provides a graph showing that the higher the diameter of prediction region, the higher the diameter of the recurrent tumor at 20 days post-PDT and lower the number of days required for the tumor to reach 100 $mm^3$ volume post-PDT. Correlation of major-axis length (mm) of regrowth region obtained from PAI prediction map in mice that underwent 1-hr DLI and had local tumor recurrence with 1. Major-axis length of recurrent tumor measured 20 days post-PDT (squares) via calipers and 2. Number of days the tumor required to reach 100 $mm^3$ after photodynamic therapy on Day 0 (circles).

The results obtained from the prediction map were validated with caliper measurements (measured by two observers blinded to the study) of the recurred tumor. The measurements were obtained 20 days post-PDT where palpable regrowth was reliably observed (FIG. 11, squares). The major axis length of the regrowth region obtained from prediction map positively correlated ($r^2$=0.84) with the recurred tumor size 20 days post-therapy, i.e., greater the predicted "nontreated" region within the tumor, greater the size of the recurred tumor. A strong negative correlation ($r^2$=0.98) was also observed between the major-axis length obtained from prediction map with the number of days taken by the tumor post-therapy (FIG. 11) to reach 100 $mm^3$. These results indicate that greater the predicted "nontreated" region where $StO_2$ did not sufficiently become hypoxic, faster the tumor regrowth rate. Tumors that had very small "notreated" regions as predicted by the PAI images, took longer to regrow back to 100 $mm^3$ and vice versa.

Discussion

The current study is motivated by the complexity of cancer biology necessitating individualized treatments for effective outcome. Prediction of response and tumor recurrence following a given therapy provides a basis for subsequent personalized treatment design and early interventions. In that context, appropriate surrogate markers could prove extremely useful. This study is a step towards this goal with the example of PDT as the treatment modality and PAI as a non-invasive, response and disease recurrence monitor in a murine model of GBM. PDT is a clinically used technique that consumes oxygen to generate cytotoxic species thus causing changes in blood oxygen saturation ($StO_2$). Here the inventors interrogated whether this change in $StO_2$ measured by PAI could be a surrogate marker for predicting treatment efficacy and tumor recurrence. PAI is a technique that can provide a 3D atlas of tumor $StO_2$ by measuring oxygenated and deoxygenated hemoglobin. The non-invasive and non-ionizing PAI provided changes in $StO_2$ due to therapy within the tumor region at ultrasonic resolution. The observation that the reduction in $StO_2$ at 6-hrs and 24-hrs post-PDT enabled identification of treatment responders from nonresponders is encouraging paving the way for investigations in other cancer models and therapies that might impact $StO_2$. The threshold-based algorithm developed using 3D tumor $StO_2$ maps allowed for also predicting of potential "tumor regrowth" areas; i.e. regions that had no significant change in $StO_2$ pre and post-therapy had local recurrence. The prediction map was obtained within 24-hours post therapy and could be used to design secondary therapeutic interventions for effective outcome. The findings of this study combined with advances and availability of PAI in clinical settings and the move toward endoscopic PAI, the results could possibly guide and monitor several treatment modalities such as PDT, radiation, anti-angiogenic therapy involving a change in $StO_2$.

Consistent with previous reports, pre-PDT and post-PDT $StO_2$ values by themselves did not predict the efficacy of the treatment. Wang et al., monitored $StO_2$ with broadband reflectance spectroscopy in tumor treated with photofrin based PDT and concluded that the absolute values of $StO_2$ were not predictive of the treatment effectiveness in tumor eradication. Wang et al., Cancer Research, 64(20):7553-61 (2004) However Wang et al. showed that the relative change in $StO_2$ immediately post-treatment is positively correlated with better treatment response. In contrast, no statistically significant difference in the mean relative-$StO_2$ values ($StO_2$ post-PDT/$StO_2$ pre-PDT) was observed. Furthermore, the relative $StO_2$ between the treated regions and regrowth regions was not statistically significant ($p>0.001$, one way ANOVA). In another study by Pham et al. significant decrease in tumor HbT and $StO_2$ was observed post therapy using frequency-domain photon migration spectroscopy BPD-PDT. Pham et al., Photochemistry and Photobiology. Wiley Online Library; 73(6):669-77 (2001). These results are at variance with the data that show tumor HbT values measured immediately before and after PDT do not have treatment prediction capability. The discrepancy with the Wang et al. and Pham et al. studies are attributed to the different types of photosensitizer used. Wang et al. utilized photofrin, while the inventors utilized BPD and different doses used, i.e., 0.5 mg/kg×100 $J/cm^2$ (100 $mW/cm^2$) with a 1-hr DLI was used by the inventors, while Pham et al. utilized 2 mg/kg×38.2 $J/cm^2$ (25 mW) dose with a 80 min DLI. Several reports have established that change in fluence rate and photosensitizer type and concentration could affect the tumor $StO_2$ and therefore affect the PDT treatment response. Busch et al., Cancer Research, 62(24):7273-9 (2002); Sitnik T M, Henderson B W., Photochemistry and Photobiology, 67(4):462-6 (1998); Busch et al. Photochem. Photobiol. Sci.; 8(12):1683 (2009). In addition, the photosensitizer uptake in the tumors could be different as Pham et al. used ovarian tumors unlike glioma tumor used in this study. Given the fact that tumors of different origin have variable PDT sensitivity and the deposited dose is a complex interaction between the PS concentration, light dose, and available oxygen, it is possible to obtain model-specific observations using PAI. Celli et al., Lasers Surg. Med., 43(7):565-74 (2011). These data suggest that comprehensive information about $StO_2$ and HbT under different illumination conditions could be a promising approach towards predictive PDT and PAI can play a major role towards this goal in understanding 3D changes in $StO_2$ and HbT at ultrasonic resolution post-therapy.

The inventors analyzed the 3D HbT maps of the mice from the recurrent tumor group to deduce if the region that regrew had different HbT levels prior to the treatment. For the group of mice that showed regrowth, The inventors plotted the HbT values at various time points in the regrowth regions (51 B-scans) and the treated regions (138 B-scans). The regrowth and treated regions within a tumor were identified based on $StO_2$ values at 6 hours and 24 hours post-PDT as shown in FIG. 10. The HbT values pre-PDT were not statistically significant in both the treated and regrowth regions within the tumor. However when the significance level is lowered to 0.05, Pre-PDT HbT in the regrowth region was significantly higher. This result points towards the possibility that the tumor regions that regrew had higher HbT, i.e., indicative of more blood volume prior to PDT and hence probably not all the vessels were completely congested due to PDT in this region. This insufficient treatment could have lead to recuperation and subsequent regrowth in this region.

Recurrences could also occur due to insufficient deposition of light dose for PDT at the boundary of the tumor. The laser beam profile used for PDT in the study has a Gaussian profile and hence sufficient light dose might not have been deposited in the tumor boundary causing insufficient treatment. Indeed a recent clinical study of PDT in Barrett's esophagus showcased that insufficient light dose did not treat the lesion completely. Pech et al., Gut 57(9), 1200-6 (2008). To evaluate the effect of light, the inventors performed PDT on mice with approximately half the tumor covered with black cloth. The prediction map clearly identified the covered part of the tumor as region not treated. However, the prediction maps also showed another region of the tumor as "nottreated". This particular region recurred post-therapy as shown in the associated photographs of the tumor showcasing the utility of PAI in identifying non-treated regions and regrowth regions.

Pogue et al. showed that tumor $pO_2$ changes due to PDT depends on several factors like photosensitizer type, light dose and DLI. Based on the type of PDT being employed, PAI performed at various time points can play a major role in PDT dosimetry by providing crucial $StO_2$ information to determine PDT treatment efficacy. Pogue et al. Comp. Biochem. Physiol., Part A Mol. Integr. Physiol., 132(1):177-84 (2002). The recent development by Ashkenazi for PAI-based tissue $pO_2$ determination is exciting and adds another dimension to the potential uses of PAI in oncology. Ashkenazi S., J. Biomed. Opt.; 15(4):040501 (2010). Utilizing multi-wavelength PAI, there is a potential to simultaneously inform changes in $StO_2$ and tumor tissue $pO_2$ for optimally designing PDT dose. Photosensitizer concentration in the tumor can be an important determinant in PDT dosimetry. Wilson et al., Lasers Med Sci., 12(3):182-99 (1997). Along with $StO_2$ and HbT, photosensitizer concentration could prove to be useful for PDT dosimetry. Zhou et al., Radiation Oncology Biology, 64(4):1211-20 (2006).

PAI could monitor photosensitizer uptake as shown by Hirao et al. and Ho et al. and the photosensitizer requires a high absorption coefficient and relatively low photobleaching tendency so as to avoid measurement induced-PDT. Hirao et al., Photochemistry and Photobiology, 86(2):426-30 (2010); Ho et al., Sci. Rep.; 4:5342-2 (2014). Dye based micro and nanoparticles such as methylene blue microbubbles (Jeon et al. J. Biomed. Opt. January 1; 19(1): 16005-5 (2014)), perfluorocarbon nanoparticles (Akers et al. ACS Nano. January 25; 5(1):173-82 (2011)) and porphysomes (Lovell et al. Nature Materials; 10(4):324-32 (2011)) are good photoacoustic contrast agents and can be used to monitor photosensitizer delivery to the tumors using PAI. Moreover, multi-modal plasmonic metal nanoagents such as photosensitizer conjugated silica coated gold nanoclusters (Huang et al., Biomaterials, 34(19):4643-54 (2013)), gold-nanocage photosensitizer conjugate (Srivatsan et al., Theranostics. 4(2):163-74 (2014)) and photosensitizer loaded gold vesicles (Lin et al., ACS Nano., 7(6):5320-9 (2013)) could be used to monitor photosensitizer uptake. Given these capabilities of PAI to monitor photosensitizer uptake and vascular damage due to PDT94, PAI can play a major role in personalizing PDT dosimetric parameters.

The current algorithm to calculate the prediction map uses a $StO_2$ threshold of 6.2% and 16.3% for 6-hrs and 24-hrs post-PDT respectively. These limits are based on the average $StO_2$ in U87 glioma tumors treated with BPD-PDT (0.5 mg/kg BPD and 100 $J/cm^2$ light dose) as shown in FIG. 7C. The responding tumors (FIG. 6) showed significant reduction in $StO_2$ and increase hypoxia 6-hrs post-PDT, i.e., the vessels are congested with no blood flow. Few studies have shown that this vascular occlusion is a slow process and need not occur immediately post PDT. Depending on the vascular status, hypoxic conditions and the pathology of the tumors, these threshold levels can be established and combined with modeling similar to that provided in this study to provide predictive calibrations for patient customized monitoring and treatment design.

In-vivo photoacoustic imaging and its biological applications have gained momentum within the past decade. Several reviews on its clinical applicability have been published. Bayer et al., Acoustics Today; 8(4):15-23 (2012). Currently, a number of research groups are moving towards translation of PAI into clinic such as endoscopic applications (Yoon T-J, Cho Y-S., World J Gastrointest Endosc. November 16; 5(11):534-9 (2013)) and intravascular applications (Wang et al., IEEE J Quantum Electron, 16(3):588-99 (2010)), in addition to breast tumor and ocular imaging. Heijblom et al., Opt Express.; 20(11):11582 (2012); Nam S Y, Emelianov S Y., Journal of the Optical Society of Korea, 18(2):151-5 (2014). It is well known that vascular targeted therapies drive the tumor towards hypoxia (i.e. lower oxygen saturation) and these changes in oxygen saturation post-treatment can be determined at ultrasonic resolution with no use of exogenous contrast agents using PAI. In view of advances and heightened interest in the clinical translatability of PAI, the results of this study are an important step towards individualized monitoring of vascular targeted therapies (e.g. PDT, radiation, anti-angiogenic).

Materials and Methods

Cell Line: Human glioblastoma cell line, U87 was obtained from American Type Culture Collection (ATCC, Rockville, Md.). Cells were cultured in Minimum Essential Medium Eagle (MEM; Mediatech, Manassas, Va.), supplemented with 10% fetal bovine serum (FBS; Life Technologies, Carlsbad, Calif.) and 1% Antibiotic-Antimycotic Solution (Mediatech, Manassas, Va.).

Animal Model: All animal experiments were approved by the Subcommittee on Research Animal Care of Massachusetts General Hospital. Female athymic Swiss nude mice (Cox, Cambridge, Mass.), 8-10 weeks old, were anesthetized with isoflurane USP (Baxter, Deerfield, Ill.) and inoculated subcutaneously with $3 \times 10^6$ U87 cells in 300 μL, of Matrigel (BD Bioscience, San Jose, Calif.). Tumor volumes were measured using calipers by two researchers separately. Tumor volume was calculated using the formula; $\pi/6 \times$ Length×Width×Height and photographs of the tumors were obtained.

Photosensitizer: Photosensitizer, benzoporphyrin derivative monoacid ring-A (BPD-MA), also known as verteporfin was obtained from USP (Rockville, Md.). Dipalmitoylphosphatidylcholine (DPPC), N-[1-(2,3-Dioleoyloxy)propyl]-N, N,N-trimethylammonium methyl-sulfate (DOTAP), cholesterol, and DSPE-PEG were obtained from Avanti Polar Lipids (Alabaster, Ala.). Liposomal formulation of BPD-MA was prepared as follows, 200 nmole of BPD-MA, 20 μmole of DPPC, 2.5 μmole of DOTAP, 10 μmole cholesterol, and 1 μmole of DSPE-PEG were mixed in roundbottom glass tube and film of the mixture was formed on the surface of glass tube by evaporating the solvent. Phosphate buffered saline (PBS) was added to dissolve the lipid film and incubated at 42° C. for 10 min followed by incubation on ice for 10 min (freeze and thaw cycle). After 5 cycles of freeze and thaw, lipid solution was warmed at 42° C. and extruded through 0.1-μm-pore filter (Whatman, Pittsburgh, Pa.) using extrusion device (Avanti Polar Lipids, Alabaster, Ala.) for 5 cycles. After the extrusion, liposomal BPD was dialyzed with dialysis membrane (MWCO=300 kD, Float-A-Lyzer 62, Spectrum Laboratories, Rancho Dominguez, Calif.) for 24-hrs. Size distribution and zeta potential were measured using dynamic light scattering (DLS; Malvern Zetasizer Nano Series; Malvern Instruments, Malvern, UK). The concentration of BPD-MA was quantified using its UV-Vis absorbance spectrum measured with Evolution 300 UV-Vis spectrometer (Thermo Fisher Scientific, Waltham, Mass.).

PDT Treatment: Mice were injected intravenously with 0.5 mg/kg of BPD-MA, then PDT was performed as follows. Mice were placed under the laser light source and covered with black cloth except tumor area. 1 or 3-hrs post injection, mice were irradiated with 100 J/cm$^2$ using a 690 nm laser diode source (Model 7401; Intense, North Brunswick, N.J.) at a fluence rate of 100 mW/cm$^2$ as measured via a VEGA laser power energy meter (Ophir Laser Measurement Group, LLC).

Fluorescence imaging: Fluorescence images of two phantom tube (500 um inner diameter) containing phosphate buffered saline (PBS) and liposomal BPD were acquired using a CRi Maestro system. A 465 nm bandpass excitation filter and a 515 nm long-pass emission filter were used. Fluorescence images at 690 nm were acquired. A custom Matlab routine was used to quantify fluorescence signals in the tubes. After fluorescence imaging, the tubes were irradiated with pulsed laser (Vevo LAZR system operating at 10 Hz repetition rate and 10 nanosecond pulse width) continuously for 15 minutes (approximately the time required to obtain 3D image of the tumor) alternately at 750 nm (45 mJ/cm$^2$ fluence) and 850 nm (36 mJ/cm$^2$ fluence). Fluorescence image of the tubes were acquired and the tubes were again irradiated with laser of the Vevo LAZR system operating at 690 nm (10 ns pulse width at 10 Hz, 44.5 mJ/cm$^2$ fluence). Fluorescence images of the tubes were acquired after pulsed laser irradiation and analyzed for photobleaching of the photosensitizer BPD.

Ultrasound and Photoacoustic Imaging: Image acquisition and quantitation was performed using the ultrasound and photoacoustic imaging system (Vevo LAZR, FUJIFILM VisualSonics, Inc.). Light generated from a tunable laser operating at either 750 nm or 850 nm was delivered through fiber optic bundles integrated into a linear array transducer (LZ-250, 21 MHz). The Oxy-Hemo feature of the Vevo LAZR software was used to acquire the oxygen-saturation images. Mice were imaged under isoflurane. Physiological status (ECG, respiration, and body temperature) of the mice was closely monitored during image acquisition sessions. 3D ultrasound and photoacoustic images were acquired at a step size of 0.152 mm. The Vevo LAZR workstation software was utilized to mark the tumor region of interest and obtain the StO$_2$ and HbT values for every B-scan. The workstation allowed export of the raw data. The raw data is processed using customized MATLAB routines and integrated with 3D visualization software AMIRA to obtain the prediction maps.

Immunohistochemistry: An overview of the immunofluorescence staining protocol used in this study is published previously by the inventors. Spring et al., J. Biomed. Opt. September 1; 18(9):096015 (2013) Briefly, for hypoxia staining, pimonidazole (Hypoxyprobe Inc) at 60 mg/kg is injected via tail vein 1-hr prior to euthanasia of the mouse. Post-euthanasia, the tumors were extracted, skin removed and embedded in optimal cutting temperature compound and kept on dry ice for solidification. A cryotome was used to cut the tumor into 5-μm-thick cryo-sections. The sections were fixed in a precooled mixture of 1:1 acetone to methanol for 15 min on ice, (2) air dried for 30 min at room temperature, and (3) washed three times for 5 minutes in PBS with gentle agitation. A blocking solution (Dako Protein Block Reagent) was applied for 1-hr at room temperature, followed by application of the antibody at ~10 μg/mL overnight at 4° C. Mouse CD31/PECAM-1 Affinity Purified Polyclonal Ab (R&D Systems Inc) and HP-Red549 (Hypoxyprobe Inc) were used for staining the microvasculature and hypoxic areas in the tumor section. The slides were washed in PBS and secondary antibody (Donkey Anti-Goat IgG NL493 Affinity Purified PAb (R&D systems Inc) was applied for 2-hrs at room temperature. Finally the slides were washed and sealed with coverslip. A whole slide scanning fluorescence imaging system (Hamamatsu NanoZoomer 2.0-RS) at 40× magnification was used to image the slides.

Statistics: Statistical analysis was performed using GraphpadPrism (La Jolla, Calif.). One-way ANOVA Tukey's multiple comparison test was used to statistically compare HbT and StO$_2$ values amongst different groups and time points. A p-value less than 0.001 was considered to be significant unless specified. Prognostic utility of the parameters StO$_2$ at 6-hrs and StO$_2$ at 24-hrs was investigated using Receiver-Operating-Curve (ROC) analysis. Specifically, tumors in the 1-hr DLI group that showed no palpable tumor by 30 days post-PDT were assigned to be a responder group (assigned value of 1) and 3-hr DLI group (non-responders) were assigned to be a non-responder group (assigned 0). Photoacoustic B-scans of the mice that had average StO$_2$ values at 6-hrs post-PDT less than 6.2% were assigned 1, else were assigned a value of 0. StO$_2$ values at 24-hrs post-PDT in all the group of mice were assigned 1 if the value was less than 16.3% else assigned 0. ROC analysis was performed using MedCalc (Ostend, Belgium) software. The inventors chose the threshold values of 6.2% and 16.3% for the StO$_2$ at 6-hrs post-PDT and 24-hrs post-PDT parameters as it represents 95% of the data obtained from the responding group (mean+ 2×standard deviation).

Figure 12:
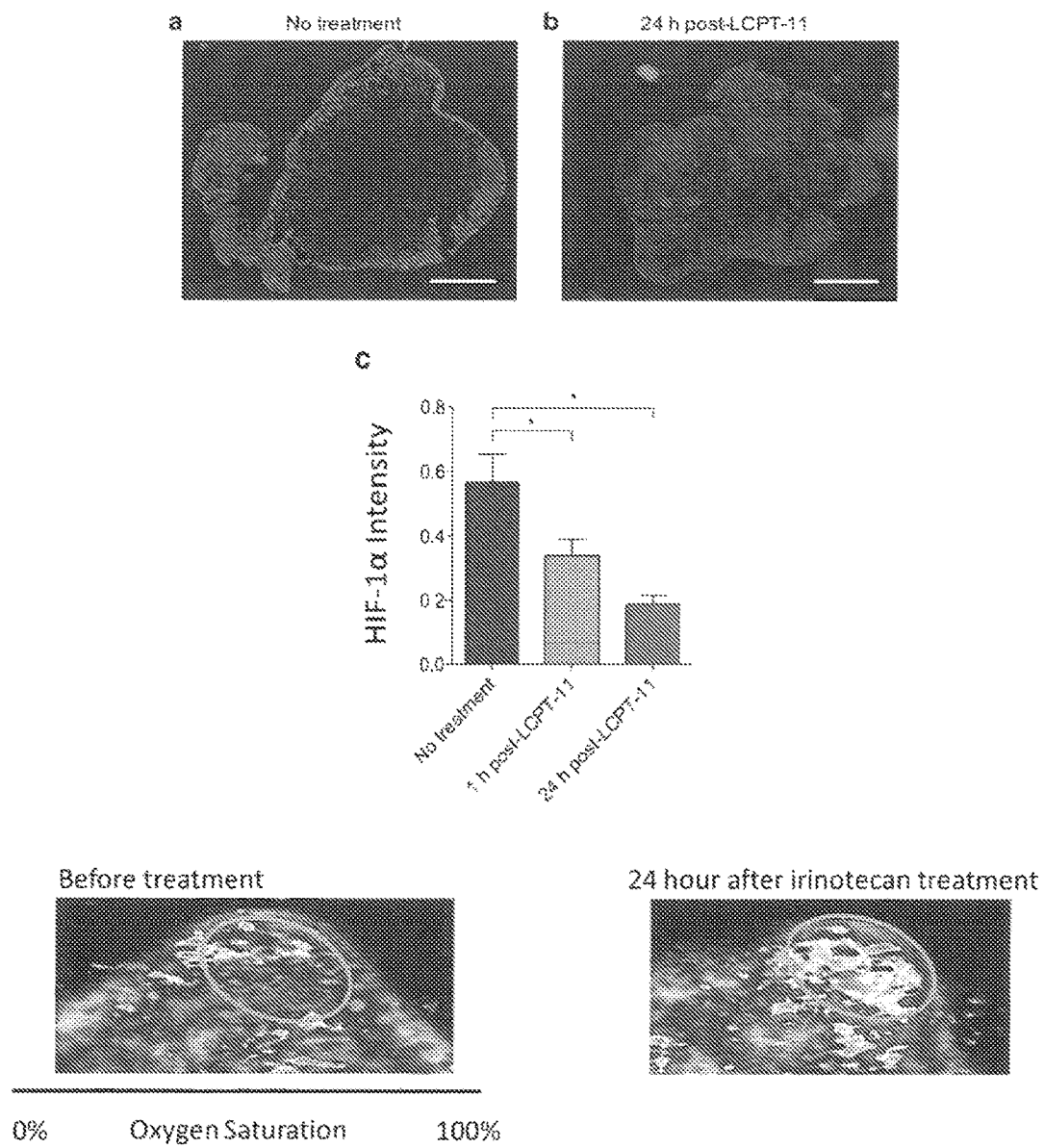
FIG. 12 provides images and a graph showing that the antitumor drug irinotecan increases tumor oxygenation. The bar graph shows that levels of hypoxia, which are inversely related to levels of tumor oxygenation, steadily increasingly decrease from 1 to 24 hours after treatment. This increase in oxygenation can be detected and utilized to predict efficacy of treatment and tumor recurrence.

Example 2: Administration of Irinotecan Reduces Tumor Hypoxia and Increases Oxygenation Detected by Photoacoustic Imaging FIG. 12 provides images and a graph showing that the drug irinotecan increases tumor oxygenation, instead of decreasing it as occurs in the case of photodynamic therapy. This increase in oxygenation can be detected and utilized to predict efficacy of treatment and tumor recurrence.

Figure 13:
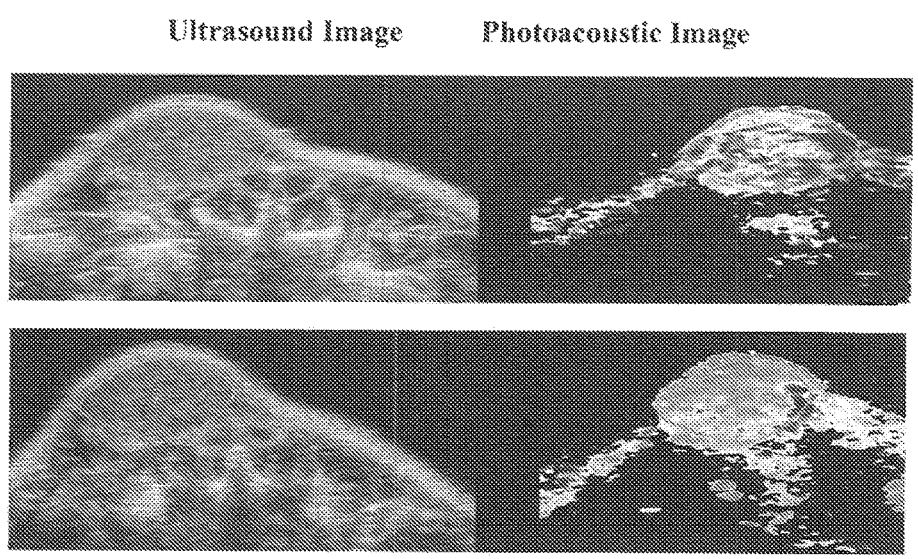
FIG. 13 provides images demonstrating the increase in oxygen saturation with very low dose PDT. The upper image shows the tumor before treatment, while the lower image shows the tumor after treatment.

FIG. 13 provides images demonstrating the increase in oxygen saturation with very low dose PDT. In our previous data sets, we showed that high dose PDT (curative dose) decrease oxygen saturation in tumors. However, when the dose is not appropriate or very low, it could increase vessel permeability and hence increase in tumor oxygenation. We show that demonstration above in subcutaneous MGG8 glioblastoma tumors. The tumor region is circled in green. Red represents highly oxygenated areas and blue represents hypoxic regions. Either an increase or decrease in oxygen saturation can be used to predict treatment efficacy and recurrence depending on the therapy. We can also predict if a particular therapy is not sufficiently administered i.e. if the dosimetry is appropriate for complete tumor destruction The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for measuring differential blood oxygen saturation in a solid tumor in a subject comprising:
    obtaining a first oxygenation image of the solid tumor before, during, or immediately after administration of vascular therapy to the solid tumor;
    obtaining a second oxygenation image of the solid tumor after a devascularization time period following administration of the vascular therapy to the solid tumor;
    determining a risk score for the solid tumor by
        spatially co-registering the first oxygenation image with the second oxygenation image,
        forming a differential image including a plurality of differential blood oxygen saturation values in a plurality of regions of the first oxygenation image and the second oxygenation image; and
        determining the risk score based on the plurality of differential blood oxygen saturation values; and
    outputting the risk score based on the differential blood oxygen saturation value for the tumor, wherein the risk score is related to at least one of a response of the solid tumor to the vascular therapy and the subject's risk of recurrence of the solid tumor based on the differential blood oxygen saturation value,
    wherein additional antitumor therapy is provided to the patient if the risk score indicates the vascular treatment is ineffective.

2. The method of claim 1, further comprising determining one or more additional tumor metabolic parameter.

3. The method of claim 2, wherein the solid tumor is contacted with one or more contrast agent before imaging.

4. The method of claim 3, wherein the one or more contrast agent is a molecular targeted contrast agent.

5. The method of claim 1, wherein the method further comprises creating a treatment map by comparing the plurality of differential blood oxygen saturation values in the differential image to a blood oxygen saturation necrosis value;
    defining region(s) of the solid tumor corresponding to regions of the images having blood oxygen saturation levels less than the blood oxygen saturation necrosis value as responder region(s); and
    defining region(s) of the solid tumor corresponding to regions of the images having blood oxygen saturation level more than the blood oxygen saturation necrosis value as potential regrowth region(s).

6. The method of claim 5, wherein the blood oxygen saturation necrosis value is obtained from a look-up table.

7. The method of claim 5, wherein the blood oxygen saturation necrosis value is a blood oxygen saturation of 16%.

8. The method of claim 1, wherein the first and second oxygenation images are obtained from non-invasive or minimally invasive imaging techniques.

9. The method of claim 8, wherein the non-invasive imaging technique is photoacoustic imaging.

10. The method of claim 1, wherein the vascular therapy comprises photodynamic therapy.

11. The method of claim 1, wherein the vascular therapy comprises a radiation therapy.

12. The method of claim 1, wherein the vascular therapy comprises administering a chemotherapeutic agent.

13. The method of claim 1, wherein the devascularization time period is between three hours and one week.

14. The method of claim 1, wherein the solid tumor is a glioma or pancreatic tumor.

15. A method for providing a prognosis of tumor recurrence in a patient, comprising
    obtaining a first oxygenation image of a solid tumor before, during, or immediately after administration of vascular therapy to the solid tumor;
    obtaining a second oxygenation image of the solid tumor after a devascularization time period following administration of the vascular therapy to the solid tumor;
    determining a differential blood oxygen saturation value by comparing the first oxygenation image and the second oxygenation image;
    comparing the differential blood oxygen saturation value to a blood oxygen saturation necrosis value to determine a risk score; and
    providing a prognosis for tumor recurrence in the patient based on the risk score, wherein the prognosis corresponds to a high likelihood of tumor recurrence when the differential blood oxygen saturation value is higher than the blood oxygen saturation necrosis value,
    wherein additional antitumor therapy is provided to the patient if the prognosis for tumor recurrence is high.

16. A method of treating a patient having a solid tumor, comprising:
    obtaining a first oxygenation image of the solid tumor before, during, or immediately after administration of vascular therapy to the solid tumor;
    obtaining a second oxygenation image of the solid tumor after a devascularization time period following administration of the vascular therapy to the solid tumor;
    determining a differential blood oxygen saturation value by comparing the first oxygenation image and the second oxygenation image;
    comparing the differential blood oxygen saturation value to a blood oxygen saturation necrosis value; and
    providing additional antitumor therapy to the patient if the differential blood oxygen saturation value is higher than the blood oxygen saturation necrosis value.

17. A method of determining the effectiveness of vascular therapy for a patient having a solid tumor, comprising:
    obtaining a first oxygenation image of the solid tumor before, during, or immediately after administration of vascular therapy to the solid tumor;
    obtaining a second oxygenation image of the solid tumor after a devascularization time period following administration of the vascular therapy to the solid tumor;
    spatially co-registering the first oxygenation image with the second oxygenation image;
    forming a differential image including a plurality of differential blood oxygen saturation values by comparing a plurality of regions of the first oxygenation image with a corresponding plurality of regions of the second oxygenation image;

comparing the plurality of differential blood oxygen saturation values in the differential image to a blood oxygen saturation necrosis value;

defining region(s) of the solid tumor corresponding to regions of the images having blood oxygen saturation levels less than the blood oxygen saturation necrosis value as responder region(s);

defining region(s) of the solid tumor corresponding to regions of the images having blood oxygen saturation level more than the blood oxygen saturation necrosis value as potential regrowth region(s); and characterizing the vascular therapy as effective where there are no potential regrowth region(s), or any potential regrowth regions have only small differences between the blood oxygen saturation levels greater than the blood oxygen saturation necrosis value, wherein additional antitumor therapy is provided to the patient if the vascular therapy is characterized as ineffective.

18. A computer software system for quantitatively prognosis of tumor recurrence comprising a non-transitory computer-readable medium in which program instructions are stored, which instructions, when read by a data processor, cause the processor to:

receive at least two three-dimensional oxygenation images of a solid tumor, wherein one of the at least two three-dimensional oxygenation images is taken before, during, or immediately after administration of vascular therapy to the solid tumor and one of the at least two three-dimensional oxygenation images is taken after a devascularization time period following administration of the vascular therapy to the solid tumor;

register the images to create a differential image comprising the difference in blood oxygen saturation between the images;

access a database comprising a blood oxygen saturation necrosis value;

create a prognostic image, wherein portions of the solid tumor having a differential blood oxygen saturation greater than the blood oxygen saturation necrosis value are visually distinguished from portions of the solid tumor having a differential blood oxygen saturation less than the blood oxygen saturation necrosis value, wherein additional antitumor therapy is provided to the patient based on the portions of the solid tumor having the differential blood oxygen saturation greater than the blood oxygen saturation necrosis.

19. The computer software system of claim 18, wherein receive at least two three-dimensional oxygenation images comprising receive at least two three-dimensional photoacoustic oxygenation images and wherein the registration is based on features from ultrasound images.

\* \* \* \* \*